US010900965B2

(12) United States Patent
Woodle et al.

(10) Patent No.: US 10,900,965 B2
(45) Date of Patent: Jan. 26, 2021

(54) METHODS AND COMPOSITIONS FOR THE DETECTION OF FC RECEPTOR BINDING ACTIVITY OF ANTIBODIES

(71) Applicant: University of Cincinnati, Cincinnati, OH (US)

(72) Inventors: E. Steve Woodle, Cincinnati, OH (US); Alin Lucian Girnita, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 69 days.

(21) Appl. No.: 15/753,651

(22) PCT Filed: Aug. 24, 2016

(86) PCT No.: PCT/US2016/048307
§ 371 (c)(1),
(2) Date: Feb. 20, 2018

(87) PCT Pub. No.: WO2017/035185
PCT Pub. Date: Mar. 2, 2017

(65) Prior Publication Data
US 2018/0259517 A1   Sep. 13, 2018

Related U.S. Application Data

(60) Provisional application No. 62/208,938, filed on Aug. 24, 2015, provisional application No. 62/263,862, filed on Dec. 7, 2015.

(51) Int. Cl.
*G01N 33/564*   (2006.01)
*G01N 33/566*   (2006.01)
(Continued)

(52) U.S. Cl.
CPC ......... *G01N 33/564* (2013.01); *C07K 16/283* (2013.01); *G01N 33/566* (2013.01);
(Continued)

(58) Field of Classification Search
CPC ........... G01N 33/564; G01N 33/56977; G01N 33/58; G01N 33/6854; G01N 33/566; G01N 2800/245; C07K 16/283
See application file for complete search history.

(56) References Cited

U.S. PATENT DOCUMENTS

| 4,900,660 A | 2/1990 | Boyle et al. |
| 5,292,641 A | 3/1994 | Pouletty |

(Continued)

FOREIGN PATENT DOCUMENTS

| EP | 2 169 404 A1 | 3/2010 |
| EP | 2 383 572 A1 | 11/2011 |

OTHER PUBLICATIONS

Abeles, (R.)D., et al., "CD14, CD16 and HLA-DR Reliably Identifies Human Monocytes and Their Subsets in the Context of Pathologically Reduced HLA-DR Expression by $CD14^{hi}/CD16^{neg}$ Monocytes: Expansion of $CD14^{hi}/CD16^{pos}$ and Contraction of $CD14^{lo}/CD16^{pos}$ Monocytes in Acute Liver Failure," Cytometry, Part A, Journal of the International Society for Advancement of Cytometry, 2012, 81A:823-834, 12 pgs.

(Continued)

*Primary Examiner* — Gailene Gabel
(74) *Attorney, Agent, or Firm* — Frost Brown Todd LLC

(57) ABSTRACT

Disclosed are kits and methods for determining the presence or absence of an antibody of interest in a biological sample of a subject. In particular, the methods may detect either pathological or beneficial antibodies. The method may include the step of contacting a biological sample from a subject with a substrate conjugated to an antigen and an Fc (Continued)

receptor operatively linked to a detectable label. Detection of the label may indicate the presence or absence of an antibody of interest.

20 Claims, 13 Drawing Sheets

(51) Int. Cl.
  *G01N 33/58* (2006.01)
  *G01N 33/68* (2006.01)
  *C07K 16/28* (2006.01)
  *G01N 33/569* (2006.01)

(52) U.S. Cl.
  CPC ....... *G01N 33/56977* (2013.01); *G01N 33/58* (2013.01); *G01N 33/6854* (2013.01); *G01N 2800/245* (2013.01)

(56) References Cited

U.S. PATENT DOCUMENTS

| | | | |
|---|---|---|---|
| 5,482,841 A | | 1/1996 | Buelow |
| 5,945,294 A | * | 8/1999 | Frank ................. G01N 33/6854 435/6.1 |
| 6,043,348 A | | 3/2000 | Lawman et al. |
| 7,262,278 B2 | | 8/2007 | Tawara et al. |
| 7,612,180 B2 | | 11/2009 | Goldenberg et al. |
| 7,897,328 B2 | | 3/2011 | Holgersson et al. |
| 8,183,039 B2 | | 5/2012 | Schmitz et al. |
| 8,304,195 B2 | | 11/2012 | Archer et al. |
| 8,815,246 B2 | | 8/2014 | TenHoor et al. |
| 9,034,656 B2 | | 5/2015 | Mehra et al. |
| 9,063,145 B2 | | 6/2015 | Lehmann |
| 9,260,520 B2 | | 2/2016 | TenHoor et al. |
| 9,790,273 B2 | | 10/2017 | Murphy et al. |
| 2005/0221424 A1 | | 10/2005 | Utku |
| 2006/0280738 A1 | | 12/2006 | Tedder |
| 2010/0261203 A1 | * | 10/2010 | Cicciarelli ........... G01N 33/564 435/7.21 |
| 2012/0192878 A1 | | 8/2012 | Toyoda |
| 2013/0130404 A1 | * | 5/2013 | Mehra .................. G01N 33/558 436/501 |
| 2014/0170168 A1 | | 6/2014 | Reiter et al. |

OTHER PUBLICATIONS

Diebolder, C.A., "Complement is Activated by IgG Hexamers Assembled at the Cell Surface," Science, 2014, 343(6176):1260-63, 10 pgs.

Haas, et al., "Banff 2013 Meeting Report: Inclusion of C4d-Negative Antibody-Mediated Rejection and Antibody-Associated Arterial Lesions," Am J Transplant, 2014, 14(2):272-283, 13 pgs.

Hamilton, R.G., et al., "Immunological methods for quantifying free and total serum IgE levels in allergy patients receiving Omalizumab (Xolair) therapy," Journal of Immmunological Methods, Aug. 2005, 303:81-91, 11 pgs.

Hidalgo, L.G., et al., "De Novo Donor-Specific Antibody at the Time of Kidney Transplant Biopsy Associates with Microvascular Pathology and Late Graft Failure," Am J Transplant, 2009, 9(11):2532-2541, 9 pgs.

Loupy, A. et al., "Complement-Binding Anti-HLA Antibodies and Kidney-Allograft Survival," N Engl J Med, 2013, 369:1215-1226, 12 pgs.

Neppert, J., et al., "Transplant rejection associated with the presence of human leucocyte antigen antibodies detected by the FcγR inhibition test but not by the lymphocytotoxicity test," Transplant Immunology, 1997, 5:45-48, 4 pgs.

O'Leary, J.G., et al., "The Role of Donor-Specific HLA Alloantibodies in Liver Transplantation," American Journal of Transplantation, 2014, 14:779-787, 9 pgs.

Sadaka, B., et al., "Clinical and investigational use of proteasome inhibitors for transplant rejection," Expert Opin Investig Drugs (Early Online), 2011, 20(11):1535-42, 8 pgs.

White, A.L., et al., "FcγRIIB as a Key Determinant of Agonistic Antibody Efficacy," In: Daeron M., Nimmerjahn F. (eds) Fc Receptors. Curr Top Microbiol Immunol., 2014, 382:355-72, 18 pgs.

Wines, B.D., et al., "Dimeric FcγR Ectodomains as Probes of the Fc Receptor Function of Anti-Influenza Virus IgG," The Journal of Immunology, 2016, 197:1507-1516, 10 pgs.

Canadian Office Action dated Apr. 8, 2019 for Application No. CA 2,996,299, 5 pgs.

European Search Report, Supplementary, and Written Opinion dated Jan. 30, 2019 for Application No. EP 16840006.7, 8 pgs.

International Search Report and Written Opinion dated Oct. 28, 2016 for Application No. PCT/US2016/048307, 11 pgs.

U.S. Appl. No. 62/208,938, filed Aug. 24, 2015.

U.S. Appl. No. 62/263,862, filed Dec. 7, 2015.

* cited by examiner

METHODS AND COMPOSITIONS FOR THE DETECTION OF FC RECEPTOR BINDING ACTIVITY OF ANTIBODIES

CROSS REFERENCE TO RELATED APPLICATIONS

This application claims priority to and the benefit of International Application No. PCT/US2016/048307, filed Aug. 24, 2016 and entitled "Methods and Compositions for the Detection of FC Receptor Binding Activity of Antibodies," which claims priority to and the benefit of U.S. Provisional Applications 62/208,938, filed Aug. 24, 2015 and entitled "Methods and Compositions for the Detection of FC Receptor Binding Activity of Antibodies" and 62/263,862, filed Dec. 7, 2015 entitled "Fc Receptor Binding Assay for Functional Assessment of HLA Antibodies: Initial Clinical Validation," the contents of which are incorporated herein in their entirety for all purposes by reference.

BACKGROUND OF THE INVENTION

Antibodies develop when the immune system encounters molecular entities that are "non-self". Antibodies have diverse functions in normal immunologic responses and in disease states that include immunomodulatory effects (both stimulatory and inhibitory) and mediation of immune injury. Antibodies may be protective, such as those that result from vaccines or infection may protect the host from subsequent pathogen exposure. Antibodies may also be pathogenic, as in autoimmune diseases where autoantibodies such as anti-platelet antibodies (in idiopathic thrombocytopenic purpura) or anti-acetyl choline receptor antibodies (as in myasthenia gravis) mediate disease. As explained below, antibodies against allogeneic HLA antigens can be pathogenic in transplant recipients during antibody mediated rejection (AMR). Interactions of antibodies with Fc receptors mediates a substantial proportion of these widely varying functions. Facilitation of the ability to assess antibody-Fc receptor interactions with in vitro assays may provide a useful means for determining clinical relevance of an antibody population.

Rejection remains a major cause of organ transplant failure. In humans, the molecular targets for rejection are a group of polymorphic cell surface proteins termed HLA antigens. Developments in the ability to detect antibodies against HLA antigens over the past several years have greatly enhanced the ability to detect and diagnose AMR. Clinical application of these technologies has resulted in widespread recognition that antibodies against donor HLA antigens (termed donor-specific antibodies (DSA)) are likely the major reason for failure of kidney transplants, and also a major cause of failure of heart, lung, and transplants (Loupy et al, N Engl J Med 2013; 369:1215-1226). Current therapies for antibody-mediated rejection (AMR) although often effective, remain suboptimal, particularly in late AMR or in chronic AMR (Sadaka et al., *Expert Opin Investig Drugs.* 2011; 11:1535-42).

HLA antibodies develop when humans are exposed to tissues or organs from a genetically dissimilar person via blood transfusion, organ transplantation, or pregnancy. HLA antibody prevalence in the general population and in the transplant candidate population are high: over 20% of healthy individuals (higher percentages occur in women because of pregnancy) and over 60% of kidney transplant candidates have HLA-antibodies. In addition, 8-25% of kidney transplant recipients will develop de novo DSAs following transplantation. When present at very high levels prior to transplantation, DSA can cause hyperacute rejection with almost immediate loss of the kidney allograft. However, hyperacute rejection is rarely observed because HLA antibodies are efficiently detected by the single HLA antigen bead assay (SAB assay) and these transplants can be avoided. Importantly, kidney (and other organ) transplants are performed regularly in the presence of lower DSA levels, and AMR risk correlates to some degree with DSA levels. Although modest advances have been made in developing therapies for preventing and treating DSA responses, acute and chronic AMR continue to occur with significant frequency in transplant recipients, thereby presenting a major barrier that limits long-term success rates.

HLA single antigen bead (SAB) assays have been developed as a means for detecting anti-HLA antibodies. HLA single antigen beads are constructed by attaching recombinant-derived HLA antigens to microbead particles. Although HLA SABs provide a means to detect anti-HLA antibodies, they do not provide a functional assessment, or rather the pathogenic or immune-protective capacity of an antibody. One approach for assessing the pathogenic potential of HLA antibodies has been the C1q assay. However, the C1q assay remains to be proven as a clinically useful tool, and is presently not broadly adopted in the transplant community. The C1q assay has also been noted to have important limitations, including its inability to detect HLA antibody function when HLA antibodies are at moderate or low concentration. Further, it is not uncommon for AMR to occur in the absence of detectable complement activation (assessed by C4d staining of renal allograft biopsies), wherein C1q assays are often negative. In this setting, AMR diagnosis requires a renal allograft biopsy with demonstration of microvascular inflammation (peritubular capillaritis (PTCitis or glomerular capillaritis) Therefore, the avoidance of invasive procedures is a need in the art.

Estimation of the functional and pathogenic potential of HLA antibodies remains an important challenge. Sensitive and early detection of pathogenic antibodies during, before, or after transplant remains a critical need in the art. Lacking in the art is a suitable assay capable of determining the pathogenic capability of HLA antibodies and/or nonpathogenic antibodies, particularly when HLA antibodies are present at low or moderate levels in the serum. The instant invention addresses one or more of the aforementioned problems in the art.

BRIEF SUMMARY OF THE INVENTION

Disclosed are methods for determining the presence or absence of an antibody of interest in a biological sample of a subject. In particular, the methods may detect either pathological or beneficial antibodies. The method may include the step of contacting a biological sample from a subject with a substrate conjugated to an antigen and an Fc receptor operatively linked to a detectable label. Detection of the label may indicate the presence or absence of an antibody of interest.

BRIEF DESCRIPTION OF THE DRAWINGS

FIG. 4, lower panel shows that moderate strength DSA are associated with marked reduction in allograft survival.

DETAILED DESCRIPTION OF THE INVENTION

Definitions/Acronyms

Figure 1A:
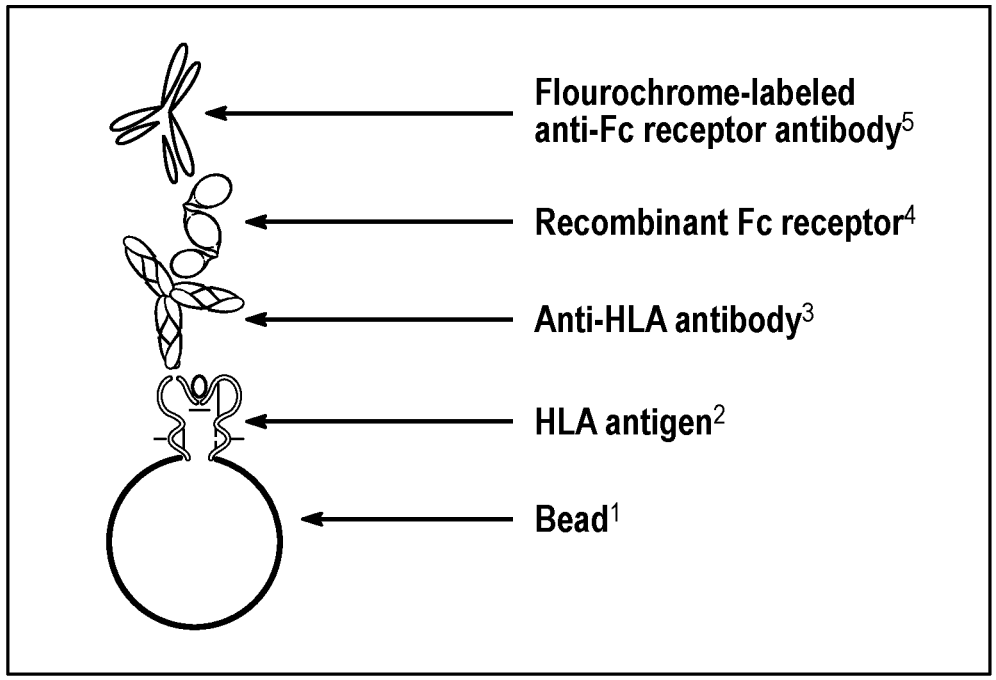
FIG. 1A depicts a diagram of the Fc receptor assay. The single HLA antigen bead (SAB) is shown expressing a recombinant derived HLA antigen. Currently available SABs from commercial vendors each express a single HLA antigen, as an example with some test reagents consisting of 98 Class I and 96 Class II unique SABs, which differ based on the HLA antigen that is expressed. Currently available SAB preparations express HLA antigens from the most frequent HLA gene loci including HLA A, HLA B, HLA C, HLA DRβ1, DRβ3/4/5, HLA DQa, HLA DQβ, DPβ, and DPα loci. Multiple unique HLA alleles may exist at each genetic locus. The anti-HLA antibody depicted in FIG. 1 derives from the serum of a patient. This in turn, binds the soluble Fc receptor (which can be the FcγR1 (CD64) molecule, or the FcγRIIa molecule (CD32A), or the FcγRIIb molecule (CD32B), or the FcγRIIc molecule (CD32c), or the FcγRIIIa molecule (CD16A), or the FcγRIIIb molecule (CD16B), or the FcµR molecule, or the DC-SIGN molecule (CD209), and which can be recombinant or patient-derived). The final step in the assay involves binding of the Fc receptor molecule by a fluorochrome-labeled anti-Fc receptor secondary antibody. The amount of bound Fc receptor may then be assayed by measuring fluorescence (most commonly on the Luminex platform (Luminex corporation, Austin, Tex.)).

ABMR/AMR—antibody-mediated rejection
B27 DSA—donor specific antibody that binds to the HLA B27 antigen.
Banff component scoring—Banff criteria consist of several components that are evaluated on the biopsy including g (glomerulitis), t (tubulitis), i (interstitial inflammation), v (endotheliitis), ptc (peritubular capillaritis), amongst others. Banff components are then used to make the diagnosis of acute cellular rejection or acute AMR, and also the grade the severity of the rejection (Haas et al, Am J Transplant 2014; 14: 272-283).
Bw4—a public epitope expressed by multiple HLA antigens from the HLA B locus. Bw4 epitope can be demonstrated on SAB and CD64 SAB assays, but not by the C1q assay.
CD16—CD16 is a 50-80 kD protein that is low affinity Fc receptor found on the surface of natural killer cells, neutrophil polymorphonuclear leukocytes, monocytes and macrophages. It can be used to isolate populations of these cells by antibodies directed towards CD16, using fluorescent-activated cell sorting or magnetic-activated cell sorting. CD16 has been identified as Fc receptors FcγRIIIa (CD16a) and FcγRIIIb (CD16b). These receptors bind to the Fc portion of IgG antibodies.
CD64—CD64 is a 72 kD single chain type I glycoprotein also known as FcγRI that possesses high affinity for IgG1 and IgG3 human antibodies. CD64 is a member of the immunoglobulin superfamily and is expressed on monocytes/macrophages, dendritic cells, and neutrophils. The expression can be upregulated by IFN-γ stimulation. CD64 also binds IgG immune complexes. CD64 plays a role in antigen capture, phagocytosis of IgG/antigen complexes, cell activation, and antibody dependent cellular cytotoxicity (ADCC).

CD32—CD32 is a surface receptor protein that binds IgG with low affinity expressed by macrophages, neutrophils, eosinophils, and platelets, CD32 may consist of the FcγRIIA (CD32A which mediates activation effects) or the FcγRIIB molecule (CD32B, which mediates immune suppressive effects) or the FcγRIIc molecule (CD32c).

C1q—The first subcomponent of the C1 complex of the classical pathway of complement activation.

CREG—Cross Reactive Groups

DSA—Donor-specific antibody

DR53—An HLA antigen encoded by the DRβ3 gene on chromosome 6.

The term "reference value" as used herein means a value which can be used for comparison with a biomarker under investigation. In one case, a reference value may be the level of a biomarker under investigation from one or more individuals without any known disease. In another case, a reference value may be the level of the biomarker in an individual's sample collected at a different time.

"Sample" or "patient sample" or "biological sample" as used herein includes biological samples such as cells, tissues, bodily fluids, and stool. "Bodily fluids" may include, but are not limited to, blood, serum, plasma, saliva, cerebral spinal fluid, pleural fluid, tears, lactal duct fluid, lymph, sputum, urine, amniotic fluid, and semen. A sample may include a bodily fluid that is "acellular". An "acellular bodily fluid" includes less than about 1% (w/w) whole cellular material. Plasma or serum are examples of acellular bodily fluids. A sample may include a specimen of natural or synthetic origin.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample; for example, the sample may be frozen at about 20° C. to about −70° C. Suitable body fluids are acellular fluids. "Acellular" fluids include body fluid samples in which cells are absent or are present in such low amounts that the peptidase activity level determined reflects its level in the liquid portion of the sample, rather than in the cellular portion. Typically, an acellular body fluid contains no intact cells. Examples of acellular fluids include plasma or serum, or body fluids from which cells have been removed.

The term "label" as used herein, refers to any physical molecule directly or indirectly associated with a specific binding agent or antigen which provides a means for detection for that antibody or antigen. A "detectable label" as used herein refers any moiety used to achieve signal to measure the amount of complex formation between a target and a binding agent. These labels are detectable by spectroscopic, photochemical, biochemical, immunochemical, electromagnetic, radiochemical, or chemical means, such as fluorescence, chemifluoresence, or chemiluminescence, electrochemiluminescence or any other appropriate means. Suitable detectable labels include fluorescent dye molecules or fluorophores. In some aspects, the detectable label may be an enzyme, a fluorescent molecule, a particle label, an electron-dense reagent, a radiolabel, a microbubble, biotin, digoxigenin, or a hapten or a protein that has been made detectable. In other aspects, the label may be an enzyme that can metabolize a substrate that results in a metabolic product that can be measured (e.g. optical density). As an example, the enzyme alkaline phosphatase can metabolize nitroblue tetrazolium (NBT) to form NBT-diformazan.

"Detecting" as used herein in context of detecting a signal from a detectable label to indicate the presence of a nucleic acid of interest in the sample (or the presence or absence of a protein of interest in the sample) does not require the method to provide 100% sensitivity and/or 100% specificity. As is well known, "sensitivity" is the probability that a test is positive, given that the person has a genomic nucleic acid sequence, while "specificity" is the probability that a test is negative, given that the person does not have the genomic nucleic acid sequence. A sensitivity of at least 50% is preferred, although sensitivities of at least 60%, at least 70%, at least 80%, at least 90% and at least 99% are clearly more preferred. A specificity of at least 50% is preferred, although specificity of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

FcR—"Fc Receptor"—Fc receptors (abbreviated FcR) are receptors that bind antibodies, classified based on the type of antibody that they recognize. For example, Fc-gamma receptors (FcγR) bind IgG, Fc-alpha receptors (FcαR) bind IgA, and Fc-epsilon receptors (FcεR) bind IgE, Fc-mu receptors (FcµR) or DC-SIGN (CD209).

HLA antigens—The human leukocyte antigens (HLA) are encoded at several gene loci on the short arm of human chromosome 6. These genes include two classes (class I and class II) that encode for proteins on the surface of cells that are responsible for regulation of the immune system in humans. Published sequences are available at https://www.ebi.ac.uk/ipd/imgt/hla/; http://hla.alleles.org and http://www.anthonynolan.org The term "operatively linked" means the linkage between two components in a way that allows a function. For example, in one aspect, a detectible label may be operatively linked to a component desired to be detected, wherein the linkage allows for detection of a detectable label bound, reversibly or otherwise, to the component of interest.

MFI—Mean Fluorescent Intensity

SAB—"Single antigen bead"

SAFR—"Single antigen Fc Receptor"

The term "subject" as used herein, refers to an animal, preferably a mammal, most preferably a human. The term subject may be interchangeably used with the term patient in the context of the present invention.

Antibodies mediate cellular and tissue injury by one or more of three mechanisms: 1) complement activation, 2) binding to Fc receptor (FcR)-bearing cells, and 3) by direct binding to cellular membrane proteins (such as HLA class I or class II molecules). For many years, the predominant mechanism for antibody effector function has been thought to be complement activation and, traditionally in transplantation, assessment of donor-specific antibody (DSA) function has been focused solely on complement activation properties. Since the discovery in 1969 that anti-HLA antibodies are lymphocytotoxic, activation of the complement cascade has been considered to be the predominant mechanism by which DSA mediate AMR. C4d, a complement split product, can be detected histologically in AMR, and C4d deposition in peritubular (and/or glomerular) capillaries is now one of the three major diagnostic criteria for AMR. A second major diagnostic criterion has been the demonstration of DSA using the SAB assay (where recombinant derived HLA antigens are bound to polystyrene beads).

Complement activation may occur via three pathways: 1) classical pathway, 2) alternative pathway, and 3) lectin-dependent pathway. Of these three pathways, the classical pathway may predominate in AMR. The classical pathway of complement activation is initiated when DSA (that are bound to HLA molecules on the cell surface) bind the complement factor C1q. Historically (and also presently) the predominant mechanism by which DSA mediate allograft injury is thought to be via complement activation. Functional assessment of DSAs to date has therefore focused exclusively on complement activation. For over four decades, anti-HLA antibody function was assessed by complement-dependent cytotoxicity assays. Over the past decade with the advent of SAB assay development, the C1q assay (available via One Lambda/ThermoFisher) was developed as a complementary assay to the SAB assay, thereby providing a mechanism for assessing complement binding capabilities of DSA.

The C1q assay is performed using patient sera and allowing these sera to react with SABs, where if present, anti-HLA antibodies will bind to the SABs. Once bound to a SAB, the ability of an anti-HLA antibody to activate complement is assayed by measuring binding of C1q. The C1q assay, however, has several known limitations including: 1) the requirement for substantial biophysical constraints to C1q binding by antibodies (the antibodies must be at high concentrations, and must be bound to target antigens and arranged in a precise hexagonal fashion), and 2) the C1q assay does not replicate in vivo complement activation, because HLA antigen expression by SABs does not accurate replicate the antigen density and biophysical properties of HLA antigens in vivo (particularly true for SABs expressing HLA DQ molecules, where the HLA DQ antigen density is much greater than in vivo). C1q assays are insensitive to HLA antibodies in low to moderate strength range, are oversensitive to DQ antibodies, often does not retain epitope patterns, and a substantial portion of rejections are complement-independent. It is known that approximately half of kidney allograft biopsies in patients with AMR do not exhibit evidence of C4d staining. C4d negative AMR is now a recognized entity within the Banff criteria for AMR diagnosis, where microvascular inflammation (peritubular capillaritis and glomerular capillaritis) can substitute for C4d staining as an AMR diagnostic criterion. Finally, recent studies have shown that relatively small changes in DSA concentration will render the C1q assay from positive to negative. In summary, the C1q assay is not completely validated as a clinically useful tool, and is presently not broadly adopted by the transplant community.

As noted above, when C4d staining is not detectable, AMR diagnosis requires demonstration of microvascular inflammation, (Haas M et al, Am J Transplant 2014; 14L272-283), which unfortunately requires an invasive biopsy procedure. Therefore, the avoidance of invasive procedures is a need in the art.

Functional assessment of HLA antibodies has historically been limited to complement-based assays. Solid phase assays assessing the classical pathway of complement activation, however, are limited in that they do not accurately reproduce biophysical constraints of C1q binding by cell surface bound antibody (Ab) (Science 2014; 343(6176): 1260). Moreover, HLA Abs are capable of inducing injury by complement-independent mechanisms, including direct signaling via class I and class II cell surface antigens, and via Fc receptor engagement. Applicant has hypothesized that comprehensive assessment of the pathogenic potential of HLA antibodies requires assessment of FcR binding capacity.

Multiple end-organ diseases benefit today from transplantation of vascular allografts: kidney, pancreas, islet, heart, lung, intestine, liver, limbs, facial grafts etc. Furthermore, non-vascular tissue grafts, such as hematopoietic and other stem cell transplantation are under substantial expansion. After transplantation, antibody-mediated rejection (ABMR) represents a major risk factor for allograft dysfunction and/or graft loss. Detection of circulating anti-HLA antibody in solid-organ transplantation has continuously improved over the past decade. Both cellular and solid-phase assays are in use for detection of anti-HLA antibodies. Multiplex and flow-based techniques are reported as most sensitive for antibody detection, followed by ELISA and CDC methods. The results of solid-phase methods seem to be less influenced by IgM, auto- and non-HLA antibodies, as well as by cytolytic protocols.

Considering the advantages and limitations of each assay, a combination, rather than a single method, may provide the best approach to determine the level of sensitization and the specificity of anti-HLA antibody in transplant recipients.

Fc receptor bearing cells have been implicated in AMR of kidney allografts, and by detecting NK cell transcripts in the allograft (as shown by Halloran (Hidalgo et al, Am J Transplant 2009; 11: 2532-2541)). The observation that approximately half of AMR episodes in kidney transplants do not appear to involve complement, suggest that the other primary mechanisms by which anti-HLA antibodies damage the allograft, viz., via Fc receptor interaction, may be of substantial importance. Until Applicant's invention, there has been no assay available to measure the Fc receptor binding capacity of HLA antibodies, nor was measurement of Fc receptor binding implicated in detection of HLA antibodies.

Disclosed herein are methods and assays for evaluating the Fc receptor binding capacity of an antibody or an antibody preparation, which, in certain aspects, may be derived either artificially (e.g., via recombinant DNA technology or hybridoma technology) or naturally (e.g., human serum or tissues). The present disclosure relates to an assay that can evaluate the pathogenic capabilities of antibodies, and/or, in other aspects, the presence of beneficial antibodies.

Pathogenic antibodies can mediate injury by one of three mechanisms: 1) direct effect on the target cell (by initiating target cell signaling via the target antigen, 2) binding Fc receptors on Fc receptor bearing cells such as macrophage or monocytes or mast cells, and 3) by activating complement. In one aspect, the instant disclosure relates to assays for evaluating the ability of a defined antibody population in human serum (e.g., antibodies that bind to beads expressing HLA A2 antigen) to bind to a defined Fc receptor or group of Fc receptors.

Fc receptors may also mediate immune protection, or downregulation of immune responses, with the classic example being the FcγRIIb receptor. The FcγRIIb receptor is known to suppress B cell function (White A L et al, Curr Top Microbiol Immunol. 2014; 382:355-72), raising the possibility that Fc receptor assays for FcγRIIb receptor binding may provide additional insights into the immunomodulatory effects of antibodies of interest.

Determining the Fc receptor binding capabilities of anti-HLA antibodies provides a mechanism for determining the potential pathogenicity or benefit of the antibodies in question, as Applicant has observed that Fc receptor bearing cells may provide an important means for mediating the effects of anti-HLA antibodies, in particular, the pathogenic effects.

When antibodies are detected, assessment of their Fc receptor binding and complement activation properties may yield important diagnostic and prognostic information. For many years, the predominant mechanism for antibody effector function has been thought to be complement activation. Traditionally, assessment of donor-specific antibody (DSA) function has been focused solely on complement activation properties. (C1q assay or Complement-dependent lymphocytotoxic assay.) Certain assays may be used to assess the ability of HLA alloantibodies to bind specific complement components (C1q as one example). However, complement binding is inherently more restrictive than Fc receptor binding in terms of the conditions required, including antigen density, antibody density, antibody concentration, antibody three dimensional orientation, and antibody affinity, as compared to Fc receptor binding.

Applicant has found that the FDA approved solid phase single antigen bead-based approaches using recombinant Fc receptor molecules have surprising advantages over traditionally used assays. Applicant has found that C1q and CD64 Fc receptor assays correlate with SAB assay, but CD64 Fc receptor assay has superior sensitivity for weak-moderate Ab strength, and that the CD64 Fc receptor assay described herein provides information unique from that of the C1q assay that is currently in use. Further, Applicant has found that the CD64 Fc receptor assay disclosed herein, correlates with histological changes in the allograft (that are used to diagnose AMR) and allograft survival. These histological changes are termed Banff component scoring. The Banff components comprise the Banff diagnostic system which is the universally accepted criteria for pathologic diagnosis of AMR, and also for acute cellular rejection. The traditionally used C1q assay does not demonstrate correlation with Banff component scoring (Haas, et al ibid). Thus, the instant disclosure offers novel and improved methods by which detection of pathogenic antibodies involved in AMR may be detected.

Figure 1B:
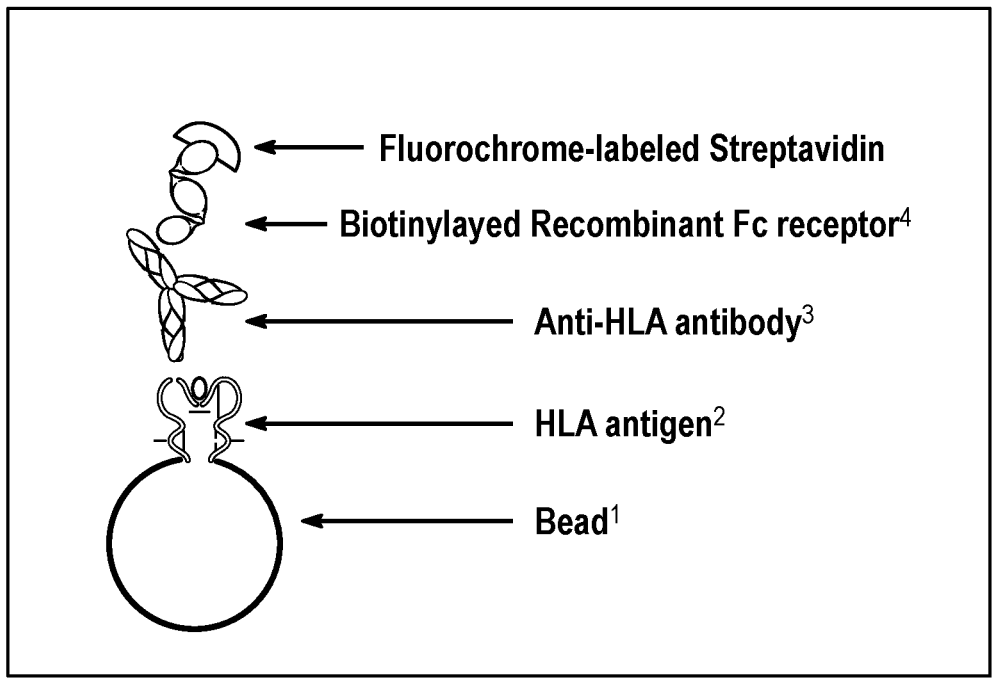
FIG. 1B depicts a schematic of the general approach underlying Example 2 using a biotinylated recombinant Fc receptor.
Figure 2:
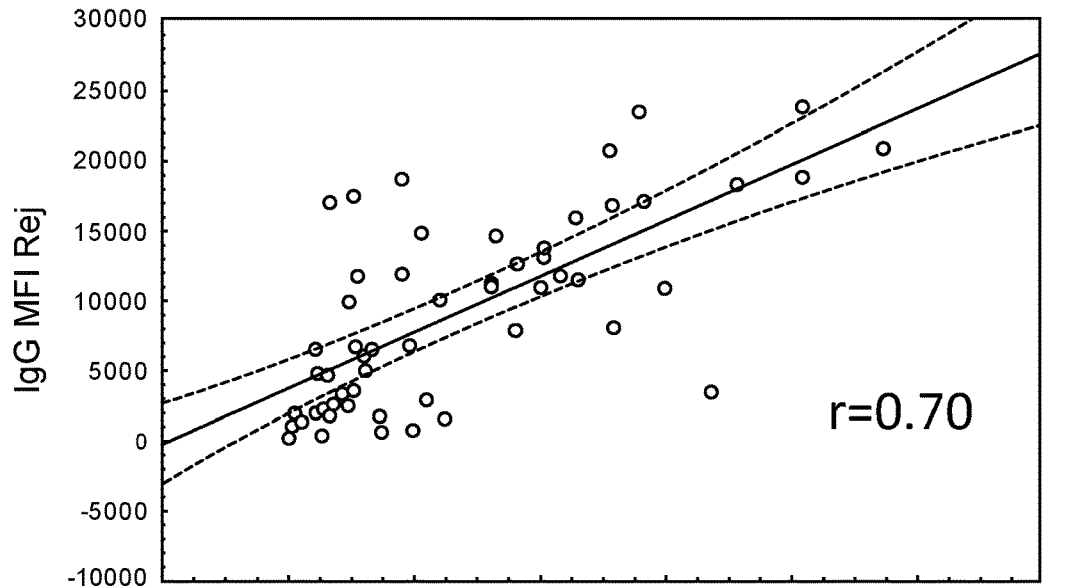
FIG. 2 depicts the correlation between the CD64 Fc receptor assay and the SAB assay (left panel) and the correlation between the C1q assay and the SAB assay (right panel). Stronger correlation with the SAB assay is observed for the CD64 Fc receptor assay than that observed for the C1q assay.
Figure 2:
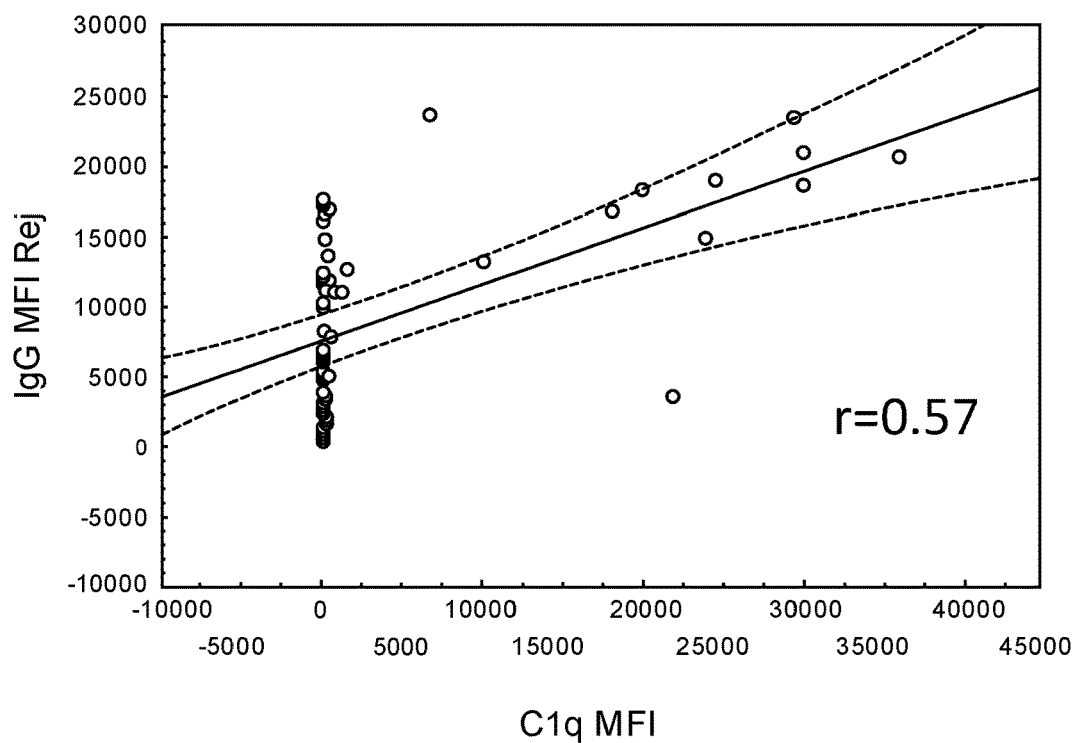
Figure 3:
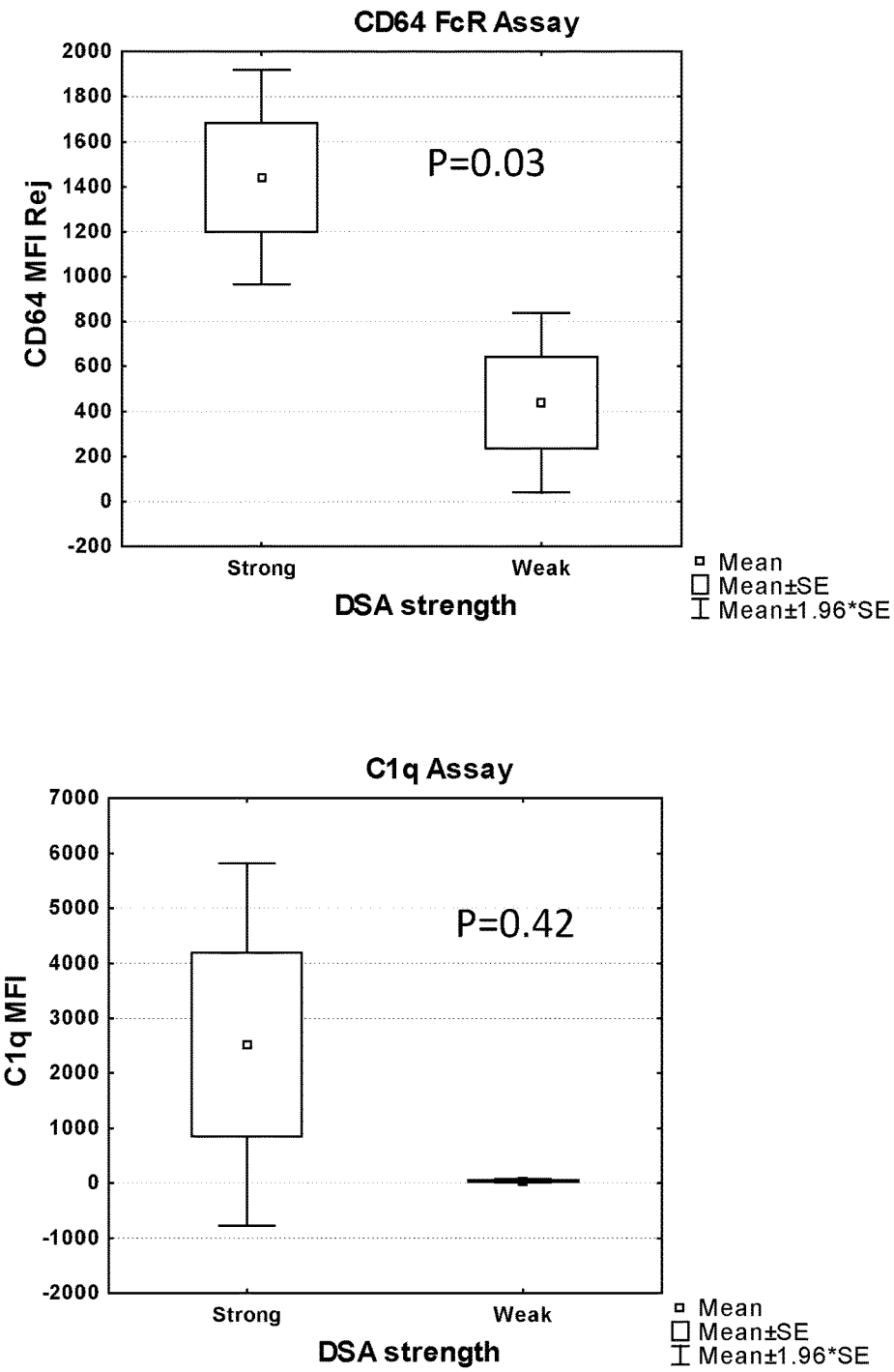
FIG. 3 depicts the abilities of the CD64 Fc receptor assay and the C1q assay to discriminate between strong (i.e., high level) DSA and weak (i.e., low level) DSA. Statistically significant differences are observed with the CD64 Fc receptor assay between strong and weak DSA but not with the C1q assay.
Figure 4:
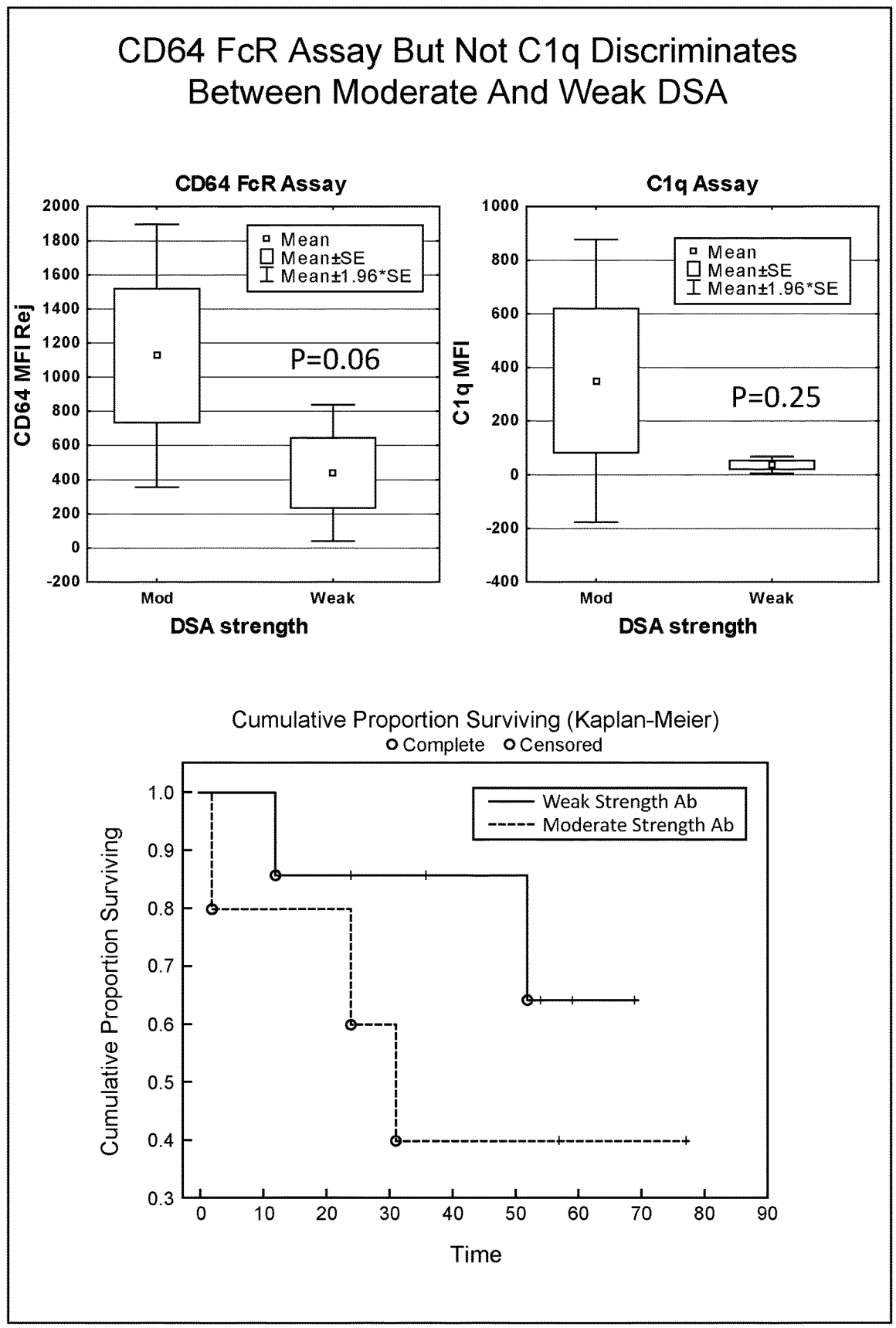
FIG. 4 depicts the abilities of the CD64 Fc receptor assay and the C1q assay to discriminate between moderate (i.e., moderate level) DSA and weak (i.e., low level) DSA. Statistically significant differences are observed with the CD64 Fc receptor assay between moderate and weak DSA but not with the C1q assay.
Figure 5:
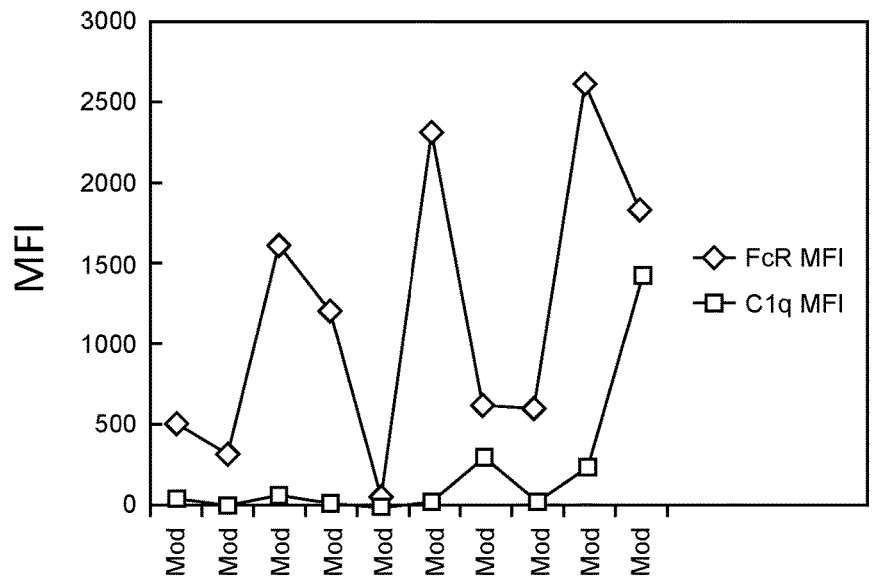
FIG. 5 depicts testing of sera from 14 patients known to have low or moderate levels (i.e., weak) of HLA antibody as determined by the SAB assay. When tested by the C1q and CD64 Fc receptor assays, C1q binding is almost universally undetectable, whereas significant CD64 Fc receptor binding is reliably detected, demonstrating the superior sensitivity of assaying for Fc receptor binding rather than C1q binding.
Figure 5:
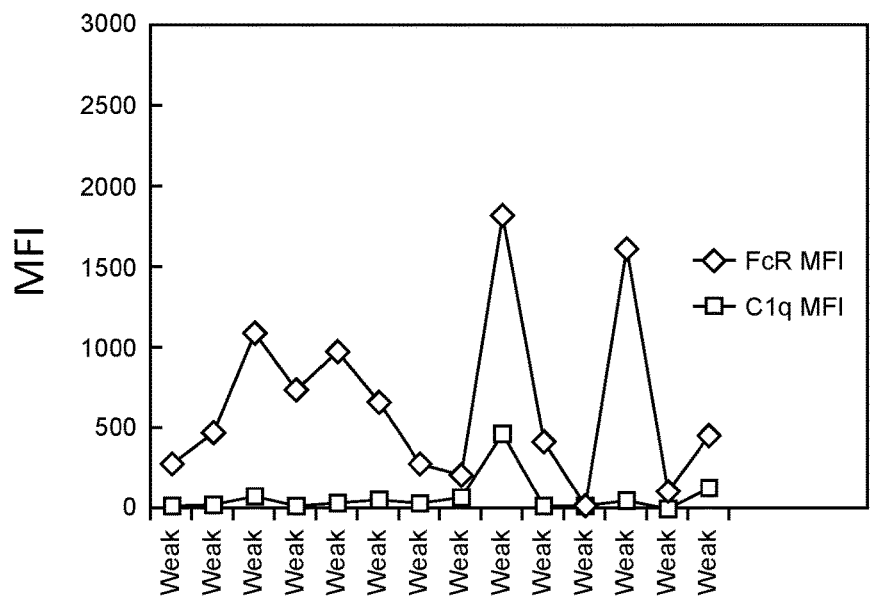
Figure 6:
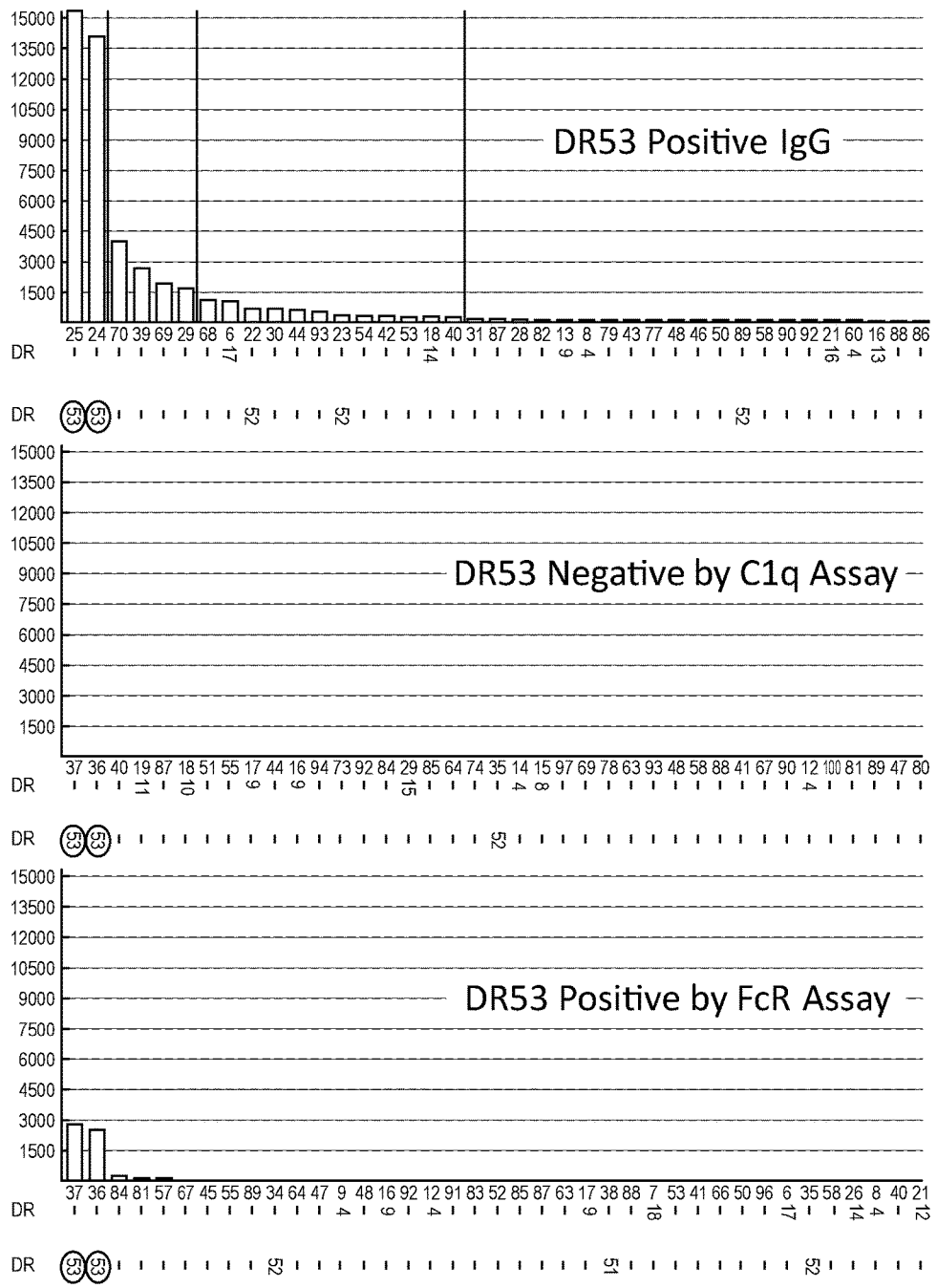
FIG. 6 depicts results of a single patient's sera tested by the SAB assay (top), the C1q assay (middle), and the CD64 Fc receptor assay (bottom). By noting the mean fluorescence intensity (MFI) on the y scale, one can see that the C1q assay does not detect binding by the DR53 antibody, which clearly binds CD64 Fc receptor.
Figure 7:
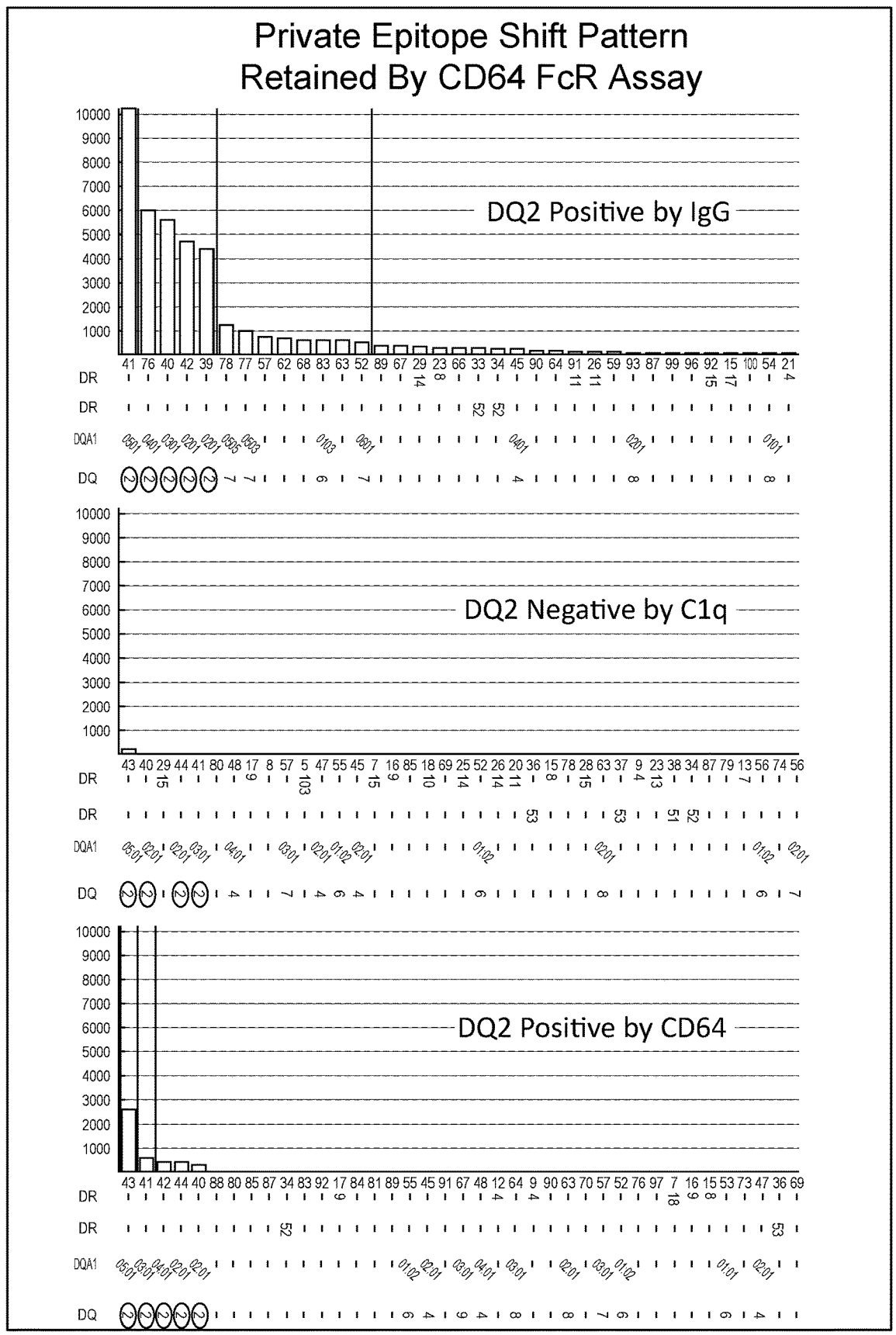
FIG. 7 depicts results of a single patient's sera tested by the SAB assay (top), the C1q assay (middle), and the CD64 Fc receptor assay (bottom). By noting the mean fluorescence intensity (MFI) on the y scale, one can see that the C1q assay does not detect binding by the DQ2 antibody, which clearly binds the CD64 receptor.
Figure 8:
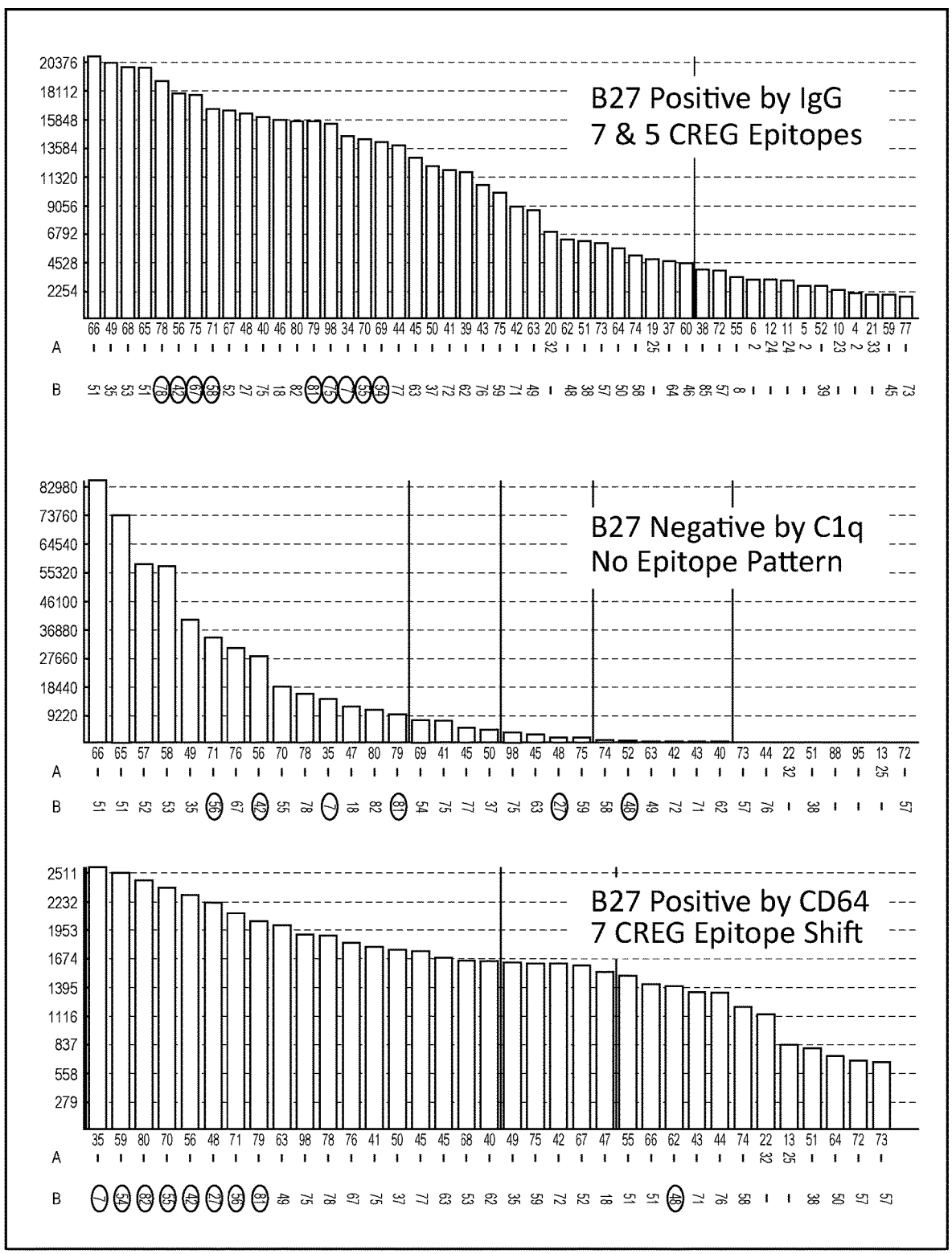
FIG. 8 depicts assay results showing that HLA antibodies bind to very small areas on the surface of a protein, which are called epitopes. Such epitopes can be expressed by several unique HLA antigens. In this figure, the patient's sera binds to an epitope on the HLA B 27 molecule, which is found in the 7 CREG group and the 5 CREG group (CREG=cross reactive groups). As one can observe in the top panel which represents the SAB assay, if the HLA antigens that are circled in blue all express a common epitope and are clustered together, therefore an epitope binding pattern is noted to have been detected. Results for the SAB assay (top), C1q assay (middle), and CD64 Fc receptor assay (bottom) demonstrate that the CD64 Fc receptor assay, but not the C1q assay, retain the epitope binding patterns detected in the SAB assay.

In one aspect, a method for determining the presence or absence of antibodies from a biological sample of a subject is disclosed. The method may comprise, for example, the step of contacting a biological sample from a subject with a substrate conjugated to an antigen with an Fc receptor operatively linked to a detectable label. Alternatively, in other aspects, the Fc receptor may be directly conjugated to a fluorochrome or alternatively to biotin, so that an avidin-based conjugate may be used for detection. See FIG. 1B.

In certain aspects, when an antibody of interest is present, a complex comprising the substrate conjugated to the antigen and the Fc receptor operatively linked to said detectable label may be formed. Detection of a detectable label on the complex may then be used to indicate that the biological sample may contain an antibody of interest, whether the antibody be pathogenic or beneficial in nature. In one aspect, the absence of detection of a label indicates the absence of an antibody of interest. The antibody of interest may be selected from pathogenic anti-HLA antibodies, non-HLA pathogenic antibodies, or a combination thereof. In one aspect, the biological sample is one in which it is suspected that the subject from which the sample is obtained is suspected of having an antibody of interest, for example, an anti-HLA antibody.

In one aspect, disclosed is an assay for assessing a level of anti-HLA antibodies in a subject. In one aspect, the assay may include a substrate, for example a substrate such as a bead with HLA antigens immobilized on the substrate that serve as an antigen source. The substrate may take a variety of forms, for example, a solid substrate. The solid substrate may be selected from the non-limiting list of beads, fibers, filters, beads, filters, fibers, screens, mesh, tubes, hollow fibers, fluidic channels, microfluidic channels, a plastic substrate, an ELISA plate, or the like.

The substrate may then be incubated with a biological sample such as test sera from a patient wherein the patient is believed or known to have anti-HLA antibodies. In one aspect, the biological sample may be obtained from a subject selected from a transplant recipient, a transplant candidate, a subject who has had a blood transfusion, a subject who is or has previously been pregnant, and a subject who has previously had an organ, tissue, or cellular transplant. The biological sample may be processed according to what is known in the art, for example, the sample may be immediately analyzed, or analyzed after storage at 4 degrees centigrade, or after storage of about −80 degrees centigrade, or after storage in liquid nitrogen. The sample may be stored for a range of time periods prior to application of the instant methods.

The substrate may then be washed, and incubated with a known recombinant derived Fc receptor (such as, for example, CD16A or CD16B, CD32A, CD32B, CD32C, or CD64) and washed a second time. The substrate may then be incubated with a secondary antibody (either a monoclonal or polyclonal antibody that is specific for the Fc receptor of interest and is labeled with a fluorochrome (or other identifiable marker)) and washed. Incubation and wash times will be readily determined by one of ordinary skill in the art, as will the various markers for labeling the antibody and also for wash solutions (most commonly phosphate buffered saline "PBS").

The substrate may then be analyzed for the presence of the detectable marker, which may take a variety of forms. For example, in one aspect, the substrate may be a bead that is analyzed in a flow cytometer (or on a Luminex platform (Luminex Corporation, Austin, Tex.) for fluorescence intensity at an appropriate wavelength for a label that contains a fluorochrome such that the fluorochrome of interest is detected. In this aspect, the intensity of the strength of the signal reflects the strength of the binding of the anti-HLA antibodies and also the strength of binding of the recombinant Fc receptor molecules to the anti-HLA antibodies.

In one aspect, the recombinant Fc receptor may be an Fc receptor expressed by an immune cell. In one aspect, the Fc receptor may be one or more recombinant Fc receptor selected from CD64, CD16A, CD16B, CD32A, CD32B, CD32C, FcµR, FcεR1, and CD23 (FcεR1I). In one aspect, the FcR may comprise CD64 (Cluster of Differentiation 64). CD64 (also known as "Fc-gamma receptor 1 (FcγRI)") is a type of integral membrane glycoprotein that binds monomeric IgG-type antibodies with high affinity. After binding IgG, CD64 interacts with an accessory chain known as the common γ chain (γ chain), which possesses an ITAM motif that is necessary for triggering cellular activation. Structurally, CD64 is composed of a signal peptide that allows its transport to the surface of a cell, three extracellular immunoglobulin domains of the C2-type that it uses to bind antibody, a hydrophobic transmembrane domain, and a short cytoplasmic tail. CD64 is constitutively found on only macrophages and monocytes, but treatment of polymorphonuclear leukocytes with cytokines like IFNγ and G-CSF can induce CD64 expression on these cells. Epitope clustering, interestingly, can be detected by the CD64 assay, but not the C1q, assay. HLA antibodies bind to distinctly small areas of HLA molecules that are termed epitopes. Moreover, individually unique epitopes may be expressed by multiple unique HLA molecules (that are encoded by unique HLA alleles at differing loci). Epitopes expressed on more than one HLA antigen are termed "public" epitopes, whereas epitopes expressed on only a single unique HLA antigen are termed "private" epitopes. In SAB assays, HLA antigens expressing a public epitope will tend to cluster together, a phenomenon that is replicated by the CD64 assay, but not the C1q assay.

In one aspect, the biological sample may be contacted to a substrate conjugated to an antigen prior to contact with said Fc receptor operatively linked to a detectable label. The antigen conjugated to the substrate may be selected from an HLA antigen, an antigen that is not an HLA antigen that evokes an antibody response against a transplanted organ or tissue, an antigen that evokes an allergic response, or a combination thereof. The substrate may be washed prior to contact with the Fc receptor operatively linked to a detectable label. The biological sample and the substrate conjugated to an antigen may then be incubated for a period of time sufficient to result in a first unit comprising said substrate operatively linked to said anti-HLA antibody. The substrate-anti-HLA complex may then be incubated with a Fc receptor operatively linked to a detectable label for a period of time sufficient to form a second unit comprising a substrate-anti-HLA complex and a Fc receptor operatively linked to said detectable label, wherein the second unit may be detectable. In this aspect, the subject may be positive for anti-HLA antibodies.

In one aspect, when an antibody of interest is detected in a donor subject, a treatment may be administered to a recipient subject who will or has received an organ, cells, or tissue from said donor subject having a antibody. The treatment may be, for example, selected from intravenous immune globulin preparations, plasmapheresis, protein A adsorption columns (or analogous columns), rituximab, obinutuzumab (or other B cell depleting agents), bortezomib, carfilzomib (or other proteasome inhibitors), anti-IL6 antibody (e.g., tocilizumab), anti-BAH-antibody (e.g., belimumab), and combinations thereof.

The disclosed methods may be used for a variety of purposes, for example, to determine the presence of HLA antibodies, to select a donor for transplantation, to identify a suitable organ recipient, to stratify damage potential of an organ recipient to a donor organ, to determine long term prognosis in a donor recipient, or to determine the effectiveness of immunosuppressive agents, wherein said immunosuppressive agent prevents development of DSA with significant damage potential. In one aspect, the assay may be used post-transplantation to determine damage potential due to antibodies, wherein, if a high damage potential is determined, the method may comprise the step of administering to a donor recipient a rejection treatment, wherein the rejection treatment may be selected from one or more of the following treatments: intravenous immune globulin preparations, plasmapheresis, protein A adsorption columns (or analogous columns), rituximab, obinutuzumab (or other B cell depleting agents), bortezomib, carfilzomib (or other proteasome inhibitors), anti-IL6 antibody (e.g., tocilizumab), anti-BAFF antibody (e.g., belimumab), and combinations thereof.

In one aspect, the assay may be used to provide additional information beyond the results of the pre-transplant single antigen bead (SAB) assay, such that individual donor specific antibodies could be assessed for their potential to mediate injury to the allograft in either acute, subacute or chronic fashion. For example, if a patient had several potential living donors against which the recipient DSA, a potential for damaging the transplanted organ would exist. The Fc receptor assay may be used to assess such risk. Similarly, the assay results may be used to make decisions on deceased donor kidneys when selecting recipients from the candidate list. In this aspect, for optimal results, one may avoid recipients with DSA determined by the assay to have substantial damage potential (against the donor organ) following transplantation.

In one aspect, the assay results could be used after transplantation to detect DSA that have damage potential. In this aspect, the assay results could aid significantly in the decision whether to treat an individual DSA when detected. Further, the assay results could be used to assess the effects of rejection treatment and thereby aid in the decision as to whether additional treatment is warranted (e.g., with plasmapheresis, IVIG, rituximab, or bortezomib).

In one aspect, the Fc receptor assay may provide prognostic information as to whether DSA that are detected in patients with good function of their transplant, who may be at increased risk for long term, chronic injury. In this aspect, the assay results could help in decision making regarding therapy.

In one aspect, the assay may be a useful biomarker for clinical trial, in that when new immune suppressive agents are developed, an agent that prevents development of DSA with significant damage potential would indicate a preferred therapeutic.

Uses for the disclosed FcR assay include, but are not limited to estimation of risk imposed by a population of anti-HLA Abs in a patient who is awaiting transplantation (aid in decision regarding desensitization, aid in decision regarding induction immunosuppression, aid in decision regarding maintenance immunosuppression); Estimation of risk imposed by DSA(s) after transplantation (with AMR, or in the absence of AMR (but is at risk for chronic allograft injury); to guide therapeutic decisions (AMR, desensitization) and in populations (kidney transplant, heart transplant, lung transplant, pancreas transplant, intestinal transplantation, liver transplantation, islet transplantation).

EXAMPLES

Figure 9:
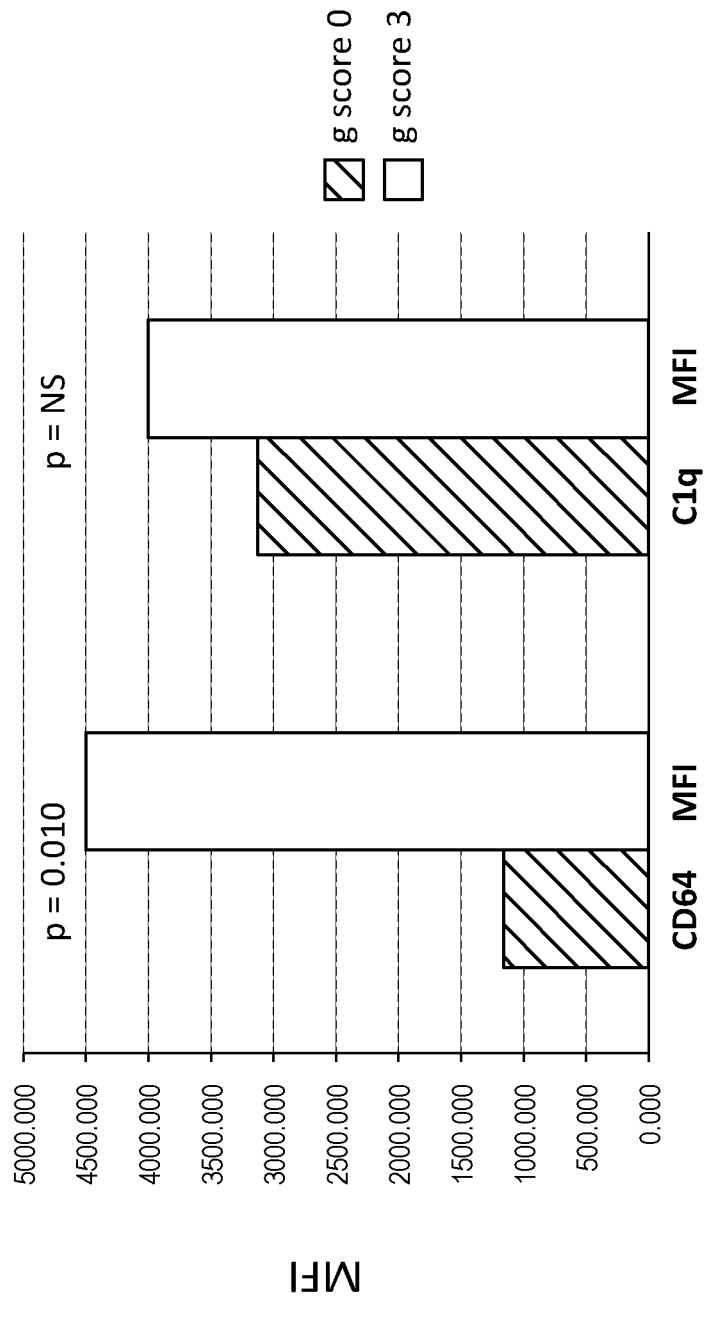
FIG. 9 depicts the relationship between patients with a Banff g score component of 0 (indicating an absence of glomerulitis on biopsy) and those with a Banff g score component of 3 (indicating severe glomerulitis on biopsy) and mean MFI values by the CD64 Fc receptor assay and by the C1q assay. These studies demonstrate that the CD64 Fc receptor assay results are more reflective of the degree of glomerulitis on kidney allograft biopsy than are C1q assay results.
Figure 10:
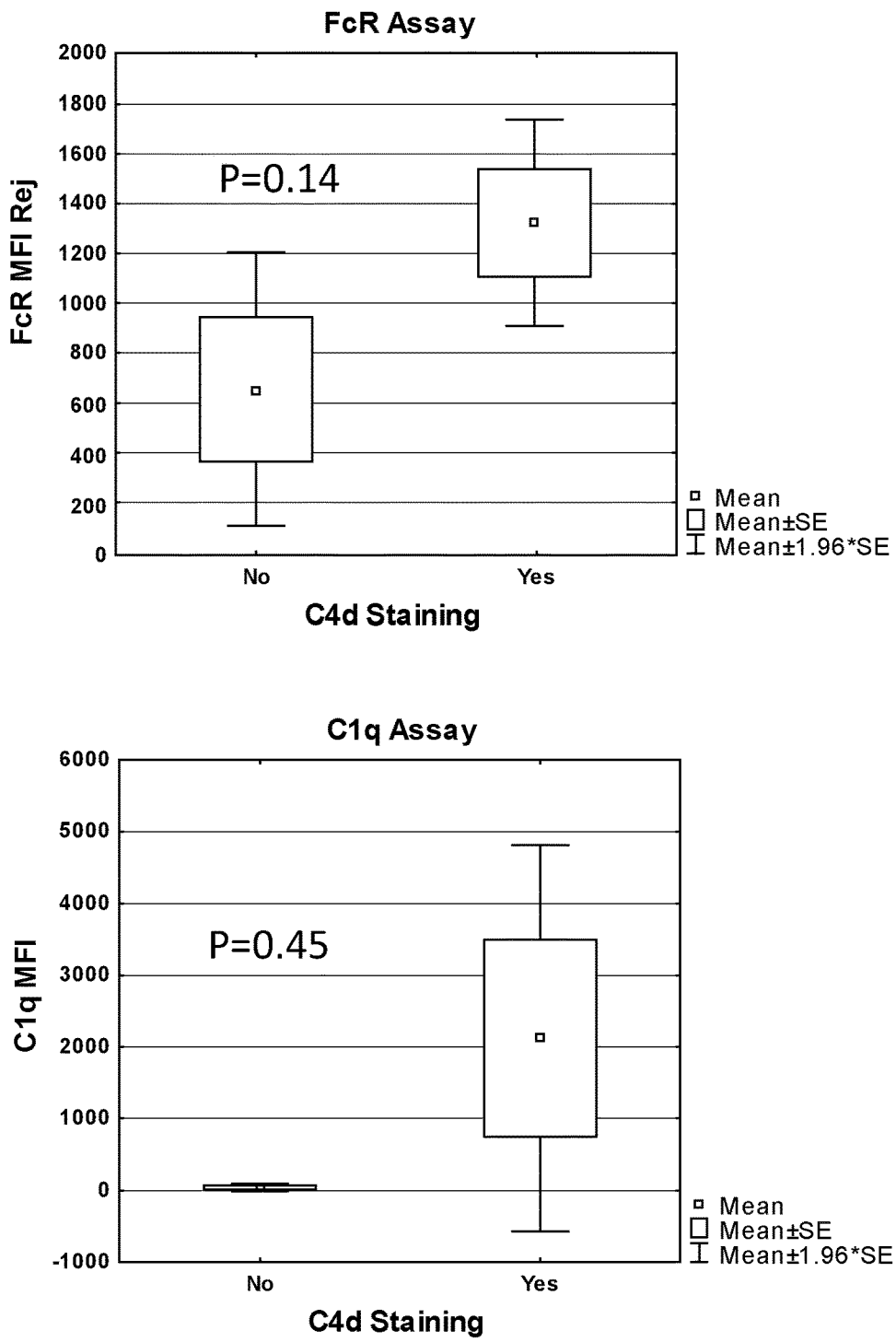
FIG. 10 shows that FcR assay may correlate better than does the C1q assay with C4d staining in biopsy-proven AMR.
Figure 11:
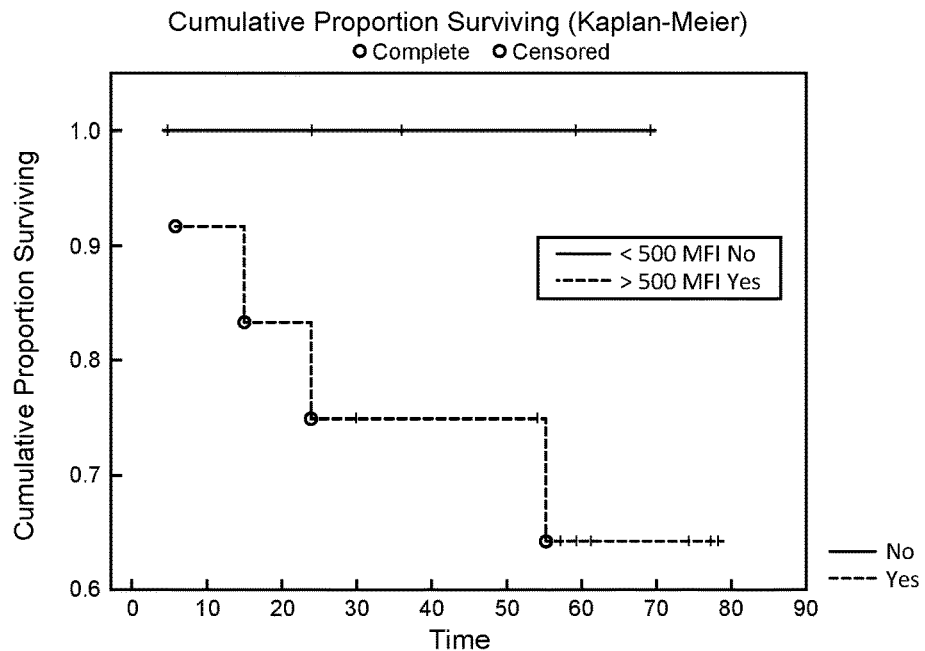
FIG. 11 shows that that renal allograft survival after early AMR correlates with the FcR Assay and not the C1q Assay.
Figure 11:
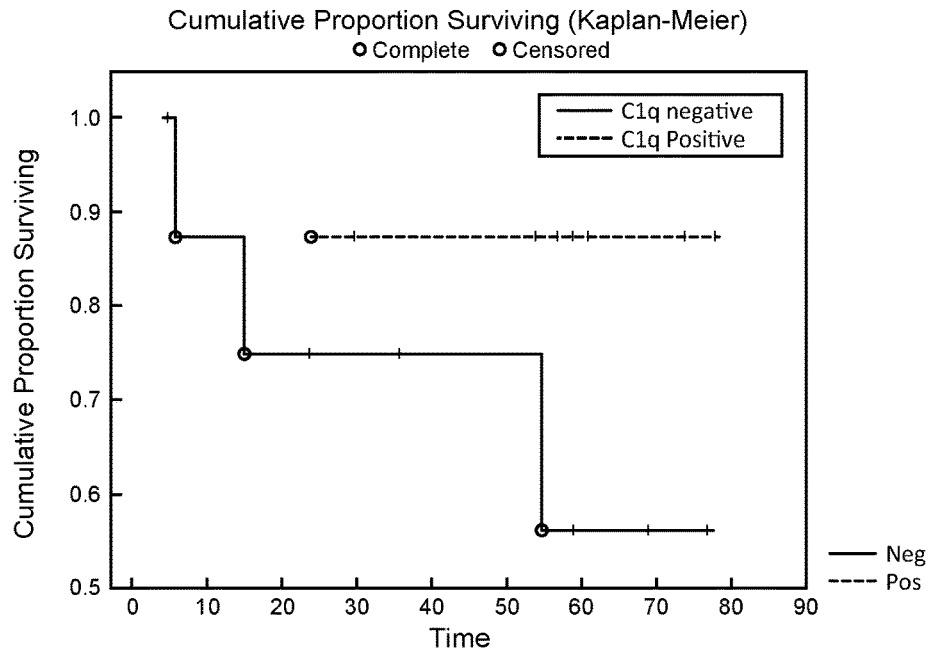
Figure 12:
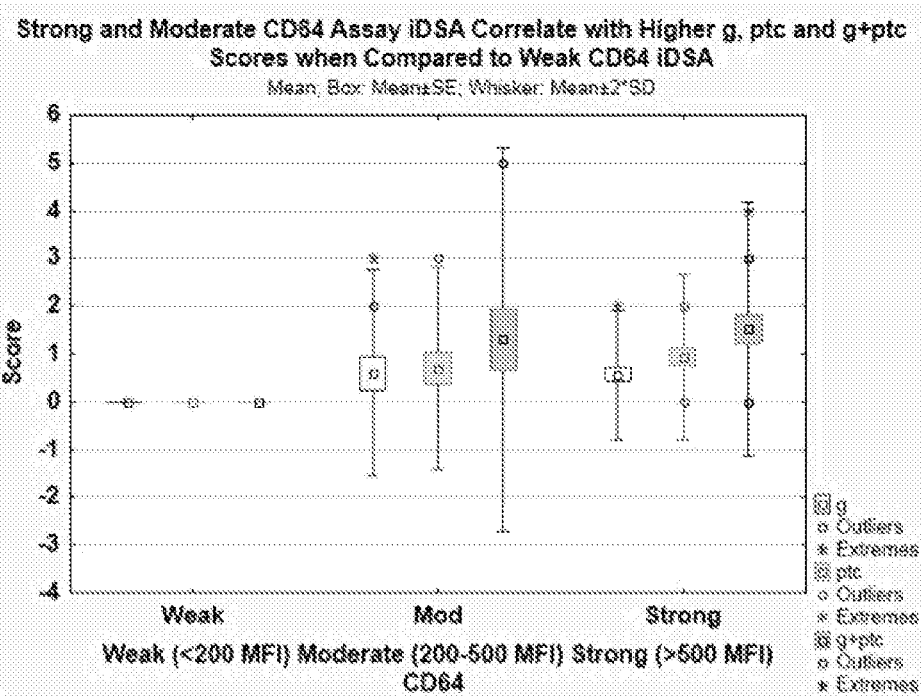
FIG. 12 depicts Banff component scores (g (glomerulitis), ptc (peritubular capillaritis), and g+ptc (composite microcirculatory inflammation) which are indicative of AMR, and how they correlate with DSA levels (weak, moderate, and strong) in the CD64 Fc receptor assay.
Figure 13:
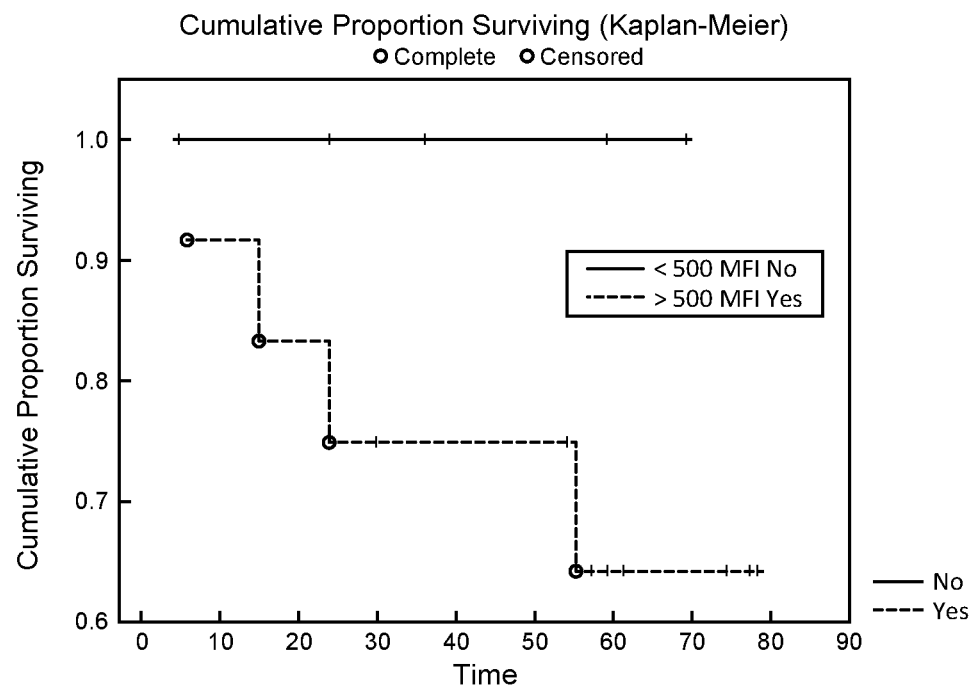
FIG. 13 depicts poorer allograft survival that is seen observed with higher MFI values in the CD64 Fc receptor assay.

In developing the CD64 FcR assay, samples were run in triplicates and analyzed on both Luminex 200 and 500 platforms. Luminex SA (Single Antigen) beads were tested (from both vendors—One Lambda/ThermoFisher and Immucor) (12 sera for validation, class 1 and II). The intra- and inter-run variability was found to be less than 10%. 60 patient sera from transplant rejection cases were tested in parallel with IgG, IgG1, IgG2, IgG3, IgG4 and C1q assays (720 tests by Luminex SA) along with 10 proficiency test samples and the 12 sera for validation. Patient data from IRB approved UC Transplant Master database was used, which included Banff histologic component scoring, Demographic data, and Renal allograft function and allograft survival data. The data showed that g (Glomerulitis) Banff Component Score in AMR correlated with FcR assay but not the C1q assay. FIG. 9.

Example 1

METHODS: After initial internal validation on PT samples, 60 patients (patients) with antibody mediated rejection (AMR) diagnosed by renal allograft biopsy constituted the study population. Pathologic data included Banff component scoring and C4d staining. Serum samples obtained prior to transplantation, at the time of AMR diagnosis and following AMR treatment were analyzed by Luminex based HLA single antigen bead (SAB) microarrays, C1q assay, IgG isotype-specific SAB assays (IgG1, IgG2, IgG3 and IgG4), and Fc Receptor (FcR) binding assay. FcR assays were performed according to standard SOPs for the laboratory-developed test.

RESULTS: FcR assay inter- and intra-run CVs were <20%. Correlation between SAB assay Ab strength and FcR assay was high (r=0.70, p=0.0075). In contrast, correlation between IgG assay and C1q assay was lower (0.57), which was primarily due to negative C1q assay results when HLA Ab strength was moderate or low, whereas assays were routinely positive. When anti-HLA-DQ specific HLA Abs were excluded, FcR assay and SAB assay correlations remained high (0.703), whereas C1q assay correlation with SAB assay declined (r-0.42). In 14 patients with AMR and low strength donor specific antibodies (DSA) (<2000MFI by SAB assay) C1q assays were routinely negative (14/14), whereas 10/14 (70%) patients were positive by assay (p=0.0004). 10 patients with AMR and moderate strength DSA (4000-8000 MFI), 1 of 10 (10%) had positive C1q assay, whereas 8/10 (80%) patients had a positive FcR assay (p=0.007). FcR assay results also positively correlated with IgG1 and IgG3 isotype-specific SAB assay strength.

Banff component acute glomerulitis (g) scoring correlated with (p=0.01), but not C1q (p=0.92) assays, with similar results for chronic glomerulitis (cg) scoring (p=0.033) C1q (p=0.49).

Analysis of death censored graft survival following AMR revealed that patients with DSA possessing weak FcR binding activity had substantially extended graft survival as compared to patients with moderate FcR binding DSA or with strong FcR binding DSA.

Conclusions: binding capacity of HLA antibodies provides information unique to that derived from SAB and C1q assays, and correlates with 1) SAB testing, 2) IgG1 and IgG3 isotype specific SAB testing, 3) g and cg Banff component scoring, and 4) death censored renal allograft survival following AMR. This initial validation analysis indicates that assessment of FcR binding capacity of HLA antibodies provides useful clinical information.

Testing Protocol: The present example is a qualitative microbead multiplex immunoassay for the in vitro diagnostic detection of Fc Receptor binding to HLA-specific antibody in serum. Measurement for the presence of FcR binding antibody is performed as an aid in transplantation patients and/or candidates with humoral allo-response. Positivity is an indicator of allo-antibody binding to FcR.

The assay is optimized for single-HLA antigen bead array. Soluble Fc receptor is commercially available and is derived from recombinant DNA technology. Fluorochrome-labeled anti-Fc receptor antibodies are commercially available either as monoclonal or polyclonal preparations.

The assay is a multiplex bead array assay based on indirect detection of protein binding. Serum is incubated with HLA-coated, internally dye-labeled microbeads. If present, circulating HLA-specific antibody will bind to corresponding epitopes of HLA antigen-coated beads. After washing, soluble recombinant Fc-gamma Receptor is then incubated with the beads. After a second wash, potentially FcR binding to the HLA-specific antibody is further tested by the anti-Fc gamma Receptor-labeled antibody, PE-fluorescence being detected by multiplex (Luminex) platform. Identification of —I binding is obtained by the analysis of fluorescence signal.

FcR binding capacity of HLA antibodies provides information unique to that derived from SAB and C1q assays. Furthermore, analysis of death censored graft survival following ABMR revealed that patients with DSA possessing weak binding activity had substantially extended graft survival as compared to patients with moderate binding DSA or with strong binding DSA.

The main conclusions of the validation studies were: a) Antibody patterns (antibody strength, specificity, class, subclass, C1q binding, Fc Receptor I binding) in early AMR are different from late AMR; b) therapeutic response is influenced by the antibody pattern.

Immediate clinical applications of antibody binding assays will be represented on the one hand by the increase in transplantability of candidates with high levels of antibodies and, on the other hand, by strategies to control the pathology mediated by antibody response against allografts.

Procedure
Method: Microarray
Instrument: LABScan 200 or LABScan 500
Analytical Principle The method is a multiplex bead array assay based on indirect detection of protein binding. Serum is incubated with HLA-coated, internally dye-labeled microbeads. If present, circulating HLA-specific antibody will bind to corresponding epitopes of HLA antigen-coated beads. After washing, soluble recombinant Fc-gamma Receptor is then incubated with the beads. After a second wash, potentially FcR binding to the HLA-specific antibody is further tested by the anti-Fc gamma Receptor-labeled antibody, PE-fluorescence being detected by multiplex (Luminex) platform. Identification of —I binding is obtained by the analysis of fluorescence signal.

Specimen Required
Serum (preferred) or Plasma (EDTA or ACD)
Specimen Type & Handling

| Criteria | |
|---|---|
| Type | |
| Preferred | Serum |
| Other Acceptable | Plasma |
| Collection Container | Red top with no additive(s) |
| Volume | |
| Optimum | 8.5 mL draw |
| Minimum | 150 µL of serum |
| Transport Container & Temperature | Red top vacutainer tube Room temperature or refrigerated |
| Stability & Storage Requirements | Room      4 days Temperature: Refrigerated:  7 days Frozen:        Indefinitely |
| Timing Considerations | Samples over 7 days old upon receipt may be unacceptable. |
| Unacceptable Specimens & Actions to Take | Fibrin may be removed from sample. Lipemic samples may be spun down and fat pulled off. |
| Compromising Physical Characteristics | Grossly hemolyzed samples are unacceptable. |
| Other Considerations | Samples should not be heat inactivated, because this might cause a high background in the test. |

Reagents and Supplies

LABScreen® Beads from One Lambda, Inc. Products are stored at −40° C. In use are thawed and stored at 2-8° C. LS1A04—LABScreen® Single Antigen HLA Class I—Combi Detection of Class I antibodies and their specificities. LABScreen® Class I Single Antigen Beads (Cat #LSP1AB04)—125 µl per vial LS2A01—LABScreen® Single Antigen HLA Class II Antibody Detection Test—Group 1; Detection of Class II antibodies and their specificities. LABScreen® Class II Single Antigen Beads—Group 1 (Cat #LSP2AB01)—125 µl per vial; LSNC—LABScreen® Negative Serum Controls LABScreen® Negative –250 µl per vial; LABScreen Wash Buffer 10× (One Lambda Inc. Cat #LSPWABSUF); Dilute to 1× Wash Buffer=12 ml buffer+108 ml of DI water; Store at 2-8° C., diluted buffer expires in 3 months. DPBS—Dulbecco's Phosphate Buffered Saline w/o Calcium or Magnesium (Lonza Cat #17-512F) Store at 2-8° C.; Anti-Human Fc gamma Receptor PE, eBioscience; Human FcR Protein (His Tag), Sino Biological Inc.; Sheath fluid Lx100 (Luminex Cat #40-50000) Store at 15-24° C.; Tray seals (One Lambda Inc. Cat # SSPSEA300); Whatman Uniplate, 96 wells, 250 µl microplate (Whatman Cat #7701-3250); Deionized water Instrumentation LABScan100/200™ or LABScan 3D Flow Analyzer; One Lambda Fusion Software; Fisher Scientific Marathon 16KM Centrifuge; Micro-centrifuge; Vortex mixer with adjustable speed Equipment Calibration Data Special instrument Requirements: Luminex Platforms (200 and 500 tested) with a reporter laser wavelength=532 nm and a classification laser wavelength=635 nm.

Device Description: The in vitro diagnostic reagent kit contains sufficient reagents for 96 samples. The reagents consist of the following: One vial lyophilized Anti-Human Fc gamma Receptor Phycoerythrin (PE), one vial Human FCGR1A Protein (His Tag) and one vial each of positive and negative controls.

Procedure

1. Thaw patient serum/plasma and centrifuge 3000 rpm for 10 minutes.
2. Vortex LABScreen® Beads and quick spin to remove from lid top.
3. Pipette 2.5 µl of appropriate LABScreen® Beads into each well.
4. Pipette 20 µl of serum into the specified well of the 96-well plate.
5. Pipette 20 µl of LSNC for each bead type. (This is used when importing into Fusion)
6. Seal the wells with a tray seal. NOTE: Use a fresh seal for each step that requires application of a tray seal.
7. Incubate for 30 minutes at room temperature 20-25 µC.
8. After incubation, add 150 µl of 1× wash buffer to each well.
9. Cover with tray seal and gently vortex. Centrifuge at 2800 rpms in Thermo IEC Centra-8R or CL40. Centrifuge for 4 minutes.
10. Remove seal from plate and flick out wash solution over trash. After flicking and while tray is still inverted, strike inverted tray 3-6 times onto a paper towel to blot.
11. Add 200 µl of 1× wash buffer to each well and repeat steps 9-10.
12. Dilute Fc gamma Receptor Protein with DPBS 1:10.
13. Add 20 µl of diluted Fc gamma Receptor Protein into each appropriate well. Gently mix each well with pipette tips and cover.
14. Incubate for 30 minutes at room temperature 20-25□C.
15. Centrifuge at 2800 rpms in IEC Centra-8R Centrifuge for 4 minutes.
16. Remove seal from plate and flick out wash solution over trash. After flicking and while tray is still inverted, strike inverted tray 3-6 times onto a paper towel to blot.
17. Add 200 µl of 1× wash buffer to each well and repeat steps 15-16 for a total of three (3) washes.
18. Dilute Anti-Human FcR PE with DPBS 1:10.
19. Add 50 µl of diluted Anti-Fc gamma Receptor PE into each appropriate well. Gently mix each well with pipette tips and cover.
20. Incubate for 30 minutes at room temperature 20-25□C.
21. After incubation, add 150 µl of 1× wash buffer to each well.
22. Cover with tray seal and gently vortex. Centrifuge at 2800 rpms in Thermo IEC Centra-8R or CL40. Centrifuge for 4 minutes.
23. Remove seal from plate and flick out wash solution over trash. After flicking and while tray is still inverted, strike inverted tray 3-6 times onto a paper towel to blot.
24. Add 200 l of 1× wash buffer to each well and repeat steps 22-23.
25. Add 80-100 l 1×DPBS to each well and mix with pipette tips in each well.
26. The sample is ready for data acquisition and analysis.

Interpretation

Internal PC shall be at least 6× the internal NC.

Results are established by comparing the FcR results to the standard PE. Review for epitopes and patterns.

Use a ratio to the positive control bead:

Bead—NC bead

PC bead—NC bead

Analytical Performance

Precision/Reproducibility: Studies were performed using 24 characterized samples and 8 samples from CAP proficiency test samples. Both vendors for Luminex SA beads were tested, for both anti-HLA class I, and anti-HLA class II reactivity.

Intra-assay variability was <20%; FcR binding assay was run in triplicates.

Inter-assay variability was <20%. Assay was performed on both on Luminex 200 and 500 platforms.

Linearity/assay reportable range: Range of results is from 0 to 10000 MFI. Internal PC must be at least 6× the internal NC. Results are established by comparing the FcR results to the standard PE, based on epitope pattern, NBG ratio (at least three times higher than NC or self the highest self-antigen bead, whatever is highest) and MFI (at least 10% of PC or the highest reactive bead in the panel, whatever is highest).

TABLE

Comparison Studies

| Sample # | Antibody Range | FcR | C1q |
|---|---|---|---|
| 1 | Strong | A2,68,69; B57,58 | A2,68,69 |
| 2 | Strong | Bw6; A33,34,66 | A2,68,69, Bw6 |
| 3 | Strong | B7,81,60,48,27,13,61 | B7,81 |
| 4 | Strong | A23, 24, 25, 32; Bw4 | A23,24 Bw4 |
| 5 | Moderate | B7,81,60,48,41,61,42,47,13,27 | NEG |
| 6 | Moderate | B57,58,8 | B57 B58 |
| 7 | Moderate | A29, B8,18,35,51,53 | NEG |
| 8 | Moderate | 12 CREG | B41, 44, 45, 46, 49, 50, 60, 61 (12CREG) |
| 9 | Weak | A2, B57,58 | NEG |
| 10 | Weak | Bw4 | NEG |

TABLE-continued

Comparison Studies

| Sample # | Antibody Range | FcR | C1q |
|---|---|---|---|
| 11 | Weak | A24, A1 | NEG |
| 12 | Weak | B44,45,76, 82; A2 | NEG |
| 13 | Strong | DR51,53; DQ2,4,7,8,9 | DR53 DQ2,4,7,8,9 |
| 14 | Strong | DR1,103,15,16, DR51 | NEG |
| 15 | Strong | DR1,7,9,10,14; DR53; DQ4,5,6,8,9 | DR7,10; DR53; DQ4,5,6,8,9 |
| 16 | Strong | DQ2, DQA1*04,05 | DQ2, DQA1*0501 |
| 17 | Moderate | DR8,11,12,13,14,17,18 | NON-SPECIFIC |
| 18 | Moderate | DR4 | NEG |
| 19 | Moderate | DR53 | NEG |
| 20 | Moderate | DQ4,8,9 | NON-SPECIFIC |
| 21 | Weak | DQ5, DP1 | NEG |
| 22 | Weak | DQ3 | NEG |
| 23 | Weak | DR17,18 DR53 | NEG |
| 24 | Weak | DR12 | NEG |
| 25 | Unknown | B: 48 60 7 81 | B: 48 60 7 |
| 26 | Unknown | A2 23 24 80 B76 | A: 23 24 80 B: 76 |
| 27 | Unknown | A1 B13 41 44 45 47 49 50 60 61 76 82 | B: 13 41 44 45 49 50 60 61 76 82 |
| 28 | Unknown | A: 2 24 68 69 B57 58 | A: 2 24 68 69; B: 54 57 58 |
| 29 | Unknown | DQ: 2 4 5 6 7 DQA: 04 05 06 | DQ: 4 5 6; DQA: 04 05 06 |
| 30 | Unknown | DR7 | NEG |
| 31 | Unknown | DR: 1 9 10 103 DRw: 51 | DR: 1 9 10 103 DR51 |
| 32 | NEG | NEG | NEG |

TABLE

Matrix Comparison
Epitope concordance in C1q verus FcR

| Antibody Range | FcR | C1q |
|---|---|---|
| Strong | 8 | 7 |
| Moderate | 8 | 2 |
| Weak | 8 | 0 |
| PT (strong) | 8 | 7 |

QC Procedures

Comparison between SAB and using well defined positive and negative sera from CAP PT. Good correlations, both for positive and negative sera. Comparison between C1q and I-binding assay using well defined positive sera from renal transplant patients with ABMR. Applicant identified 35 patients with antibody mediated rejection (ABMR: 11 early–EAMR+24 late–LAMR). DSA levels were determined at Day 0 and Day 50 after renal transplantation. All patients had at least 9 months of follow-up after ABMR therapy. The IgG1-4-specific antibody was obtained from SouthernBiotech. All cases had DNA typing for HLA-A, B, C, DRB1,3,4,5, DQA1, DQB1, DPB1 loci and negative flow T- and B-cell crossmatches. All samples were tested for the DSA detection (single-antigen beads Luminex) and post-therapeutic dynamics by IgG1-4 subtype and the disclosed methods. For comparison, all these 70 samples were tested with the commercially available C1q binding assay. Applicant compared results in 33 donor-specific antibody DSAs for early ABMR, and 52 for late ABMR and compared 21 preformed DSAs and 64 de novo DSA. The assay results of the instant disclosure were correlated with results from the C1q binding assay, IgG subtype binding assay, public epitope clustering and histo-pathological rejection scores. Correlation between C1q and MFI values (R=0.5, p<0.05).

It can be noticed that FcR MFI <2500 are negative by C1q, which demonstrates higher sensitivity for Applicant's assay. C1q and assays correlate with SAB assay, but FcR has superior sensitivity for weak-moderate Ab strength.

Example 2. Biotin-Conjugated Protein (CD64) Assay (See FIG. 1B)

Reagents
Anti-Human CD64 (Fc gamma Receptor 1) PE, eBioscience #12-0649 (Concentration: 5 uL (0.25 µg)/test Clone 10.1 mouse IGG1 0; Human CD64/FCGR1A Protein (His Tag), Sino Biological Inc. #10256-H08H (recommended 380 µl of sterile water added to vial); Human CD64.FCGR1 Protein His & AVI Tag, Biotinylated; Sino Biological Inc. #10256-H27H-B; Anti-Human PE Streptavidin; eBioscience #12-4317-87.

2—Step Biotin
1. Add serum 25 µL and beads 1.8 µL.
2. Incubate for 30 minutes, room temp on shaker
3. Using LabScreen Wash Buffer, perform 3 washes (4 min @ 2800 rpm)
4. Add 20 µL of CD64-biotin conjugated protein @ 1:10
5. Add 20 µL of Streptavidin-PE @ 1:10
6. Incubate for 30 minutes, rm temp
7. Using LabScreen Wash Buffer, perform 2 washes
8. Add 80 µL DPBS and run on Luminex 3—Step-Classic CD64 Protein
1. Add serum and beads.
2. Incubate for 30 minutes, room temp in dark on rocker (3-4 min @ 2800 rpm)
3. Using LabScreen Wash Buffer, perform 2 washes
4. Add 20 uL of CD64 at dilution of 1:10 using DBPS
5. Incubate for 30 minutes, room temp
6. Using LabScreen Wash Buffer, perform 3 washes (3-4 min @ 2800 rpm)
7. Add 50 uL of CD64-PE at 1:10 using wash buffer
8. Incubate for 30 minutes, rm temp
9. Perform 2 washes (3-4 min @ 2800 rpm)
10. Add 80 µL DPBS and run on Luminex Example 3

Serum is collected from a transplant recipient in a tube where blood is allowed to form thrombus. Serum is separated from the clot by centrifugation. 50 µL of serum is combined with 5 µL single HLA antigen beads (from either Immucor or One Lambda/Thermo Fisher. The serum and beads are incubated for 30 minutes at room temperature. Two washes are performed with a wash buffer (as provided by the manufacturer). 50 µL of recombinant CD64, diluted 1:50 in wash buffer (usually phosphate buffered saline) is added, and incubation performed for 30 minutes at room temperature. The beads are then washed three times using the wash buffer. 50 µL of PE conjugated murine anti-human CD64 antibody (BioLegend) at a dilution of 1:50 is added, followed by a 30-minute room temperature incubation. The beads are washed one time with wash buffer. 80 µL of wash buffer is added to the beads and beads are then analyzed on the Luminex platform.

In other aspects, other Fc receptor molecules may be used for analysis including: 1) FcγRIIIa (CD16A), 2FcγRIIIb (CD16B), 2) FcγRIIa (CD32A), 3) FcγRIIb (CD32B), 4) FcγRIIc (CD32C), 5) FcµR, 6) FcεRI, 6) FcεRII, 7) FcαR, or 7) DC-SIGN. Alternatively, an FcR preparation may be derived from a patient (via a process such as immunoprecipitation) and the individual patients FcRs may be used in the assay rather than the recombinant FcR. In one aspect, rather than use a secondary antibody to the recombinant Fc receptor, one may directly conjugate the fluorescent marker (or a molecule such as biotin, where an avidin-linked fluorochrome (or other marker) may be added) directly to the recombinant Fc receptor.

Example 4

Serum is collected from a transplant recipient in a tube where blood is allowed to form thrombus. Serum is separated from the clot by centrifugation. 50 µL of serum is combined with 5 µL single HLA antigen beads (from either Immucor or One Lambda/Thermo Fisher. The serum and beads are incubated for 30 minutes at room temperature. Two washes are performed with a wash buffer (as provided by the manufacturer). 50 µL of recombinant CD16, appropriately diluted in wash buffer (usually phosphate buffered saline) is added, and incubation performed for 30 minutes at room temperature. The beads are then washed three times using the wash buffer. 50 µL of PE conjugated murine anti-human CD16 antibody is added at appropriate dilution, followed by a 30-minute room temperature incubation. The beads are washed one time with wash buffer. 80 µL of wash buffer is added to the beads and beads are then analyzed on the Luminex platform.

Example 5

Serum is collected from a transplant recipient in a tube where blood is allowed to form thrombus. Serum is separated from the clot by centrifugation. 50 µL of serum is combined with 5 µL single HLA antigen beads (from either Immucor or One Lambda/Thermo Fisher. The serum and beads are incubated for 30 minutes at room temperature. Two washes are performed with a wash buffer (as provided by the manufacturer). 50 µL of recombinant FcγRIIb, diluted appropriately in wash buffer (usually phosphate buffered saline) is added, and incubation performed for 30 minutes at room temperature. The beads are then washed three times using the wash buffer. 50 µL of PE conjugated murine anti-human FcγRIIb antibody is added at appropriate dilution, followed by a 30-minute room temperature incubation. The beads are washed one time with wash buffer. 80 µL of wash buffer is added to the beads and beads are then analyzed on the Luminex platform.

Example 6

Exemplary protocol for a CD64 assay using a patient's own Fc Receptors in lieu of a recombinant Fc receptor. As an alternative to using a recombinant Fc receptor (such as CD64), the assay may be personalized by using an individual patients own Fc receptors as follows: 1. Patient's blood may be drawn and a Ficoll separation performed to isolate mononuclear cells. 2. A lineage specific cell isolation (for example, NK, monocytes-macrophages, lymphocytes, etc.) may be performed. 3. Mononuclear cells may be lysed using a non-denaturing lysis buffer 4 Immunoprecipitation may be performed by incubating overnight at 4° C. an anti-Fc receptor antibody (polyclonal or monoclonal, that targets the Fc receptor of interest) with the cell lysate. 5. Incubate with sepharose beads coupled to protein A or protein G (based on the Ig subtype of the anti-Fc receptor antibody). 6. Elute the captured Fc receptor for use in an Fc receptor assay.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm"

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for determining the presence or absence of an antibody of interest in a post-transplant biological sample of a donor recipient subject who has received an organ, cells or tissue from a donor subject to determine post-transplantation damage potential to said organ, cells or tissue caused by contact of said organ, cells or tissue from said donor subject with said antibody of interest, the method comprising contacting said biological sample from said donor recipient subject with:
   a. a substrate conjugated to an antigen of said donor subject; and
   b. an Fc receptor operatively linked to a detectable label; wherein:
   (1) said antibody of interest is selected from the group consisting of pathogenic anti-HLA antibodies, non-HLA pathogenic antibodies, non-HLA protective antibodies and combinations thereof;
   (2) when said pathogenic and/or protective antibody of interest is present in said post-transplant biological sample, said pathogenic and/or protective antibody of interest binds to and forms a complex with each of said substrate conjugated to said antigen of said donor recipient subject and said Fc receptor operatively linked to said detectable label; and (3) detection of said detectable label on said complex indicates that said post-transplant biological sample contains said pathogenic and/or protective antibody of interest;

and further wherein, when said pathogenic and/or protective antibodies are detected in said post-transplant biological sample, the method further comprises administering to said donor recipient subject a treatment that is effective to treat or prevent damage to said post-transplantation organ, cells or tissue of said donor recipient subject, said method comprising a step selected from the group consisting of administering to said donor recipient subject intravenous immune globulin preparations, a B cell depleting agent, a proteasome inhibitor, an anti-IL6 antibody, an anti-BAFF antibody and combinations thereof.

2. The method of claim 1, wherein an absence of detection of said detectable label indicates an absence of said complex in said post-transplant biological sample.

3. The method of claim 1, wherein said post-transplant biological sample is suspected of having anti-HLA antibodies.

4. The method of claim 1, wherein said substrate is a solid substrate.

5. The method of claim 1, wherein said Fc receptor is a recombinant Fc receptor expressed by an immune cell.

6. The method of claim 1, wherein said Fc receptor is one or more recombinant Fc receptors selected from the group consisting of CD64, CD16A, CD16B, CD32A, CD32B, CD32C, FcαR, FcµR and DC-SIGN.

7. The method of claim 1, wherein said post-transplant biological sample is contacted to said substrate conjugated to said antigen of said donor recipient prior to contact with said Fc receptor operatively linked to said detectable label.

8. The method of claim 7, wherein said post-transplant biological sample contacted to said substrate conjugated to said antigen is washed prior to further contact with said Fc receptor operatively linked to said detectable label.

9. The method of claim 1, wherein said detectable label is biotin or a fluorochrome.

10. A kit for determining the presence or absence of an antibody of interest in a biological sample of a subject, comprising
   a. a substrate conjugated to an antigen; and
   b. an Fc receptor operatively linked to a detectable label, wherein said Fc receptor is selected from the group consisting of CD64, CD16A, CD16B, and DC-SIGN;
wherein:
   (1) said antibody of interest is capable of forming a complex with each of said substrate conjugated to said antigen and said Fc receptor operatively linked to said detectable label;
   (2) detection of said detectable label on said complex can be used to determine the presence of pathogenic antibodies in said sample; and
   (3) wherein said antibody of interest is selected from the group consisting of pathogenic anti-HLA antibodies, non-HLA pathogenic antibodies, non-HLA protective antibodies and a combination thereof.

11. The kit of claim 10, wherein said Fc receptor is a recombinant Fc receptor expressed by an immune cell.

12. The kit of claim 10, wherein said detectable label is biotin or a fluorochrome.

13. A method for identifying a suitable donor subject to donate an organ, cells or tissue to a pre-transplant recipient subject, the method comprising contacting a biological sample from said donor subject with:
   a. a substrate conjugated to an antigen of said pre-transplant donor recipient subject; and
   b. an Fc receptor operatively linked to a detectable label, wherein said Fc receptor is selected from the group consisting of CD64, CD16A, CD16B, and DC-SIGN;
wherein:
   (1) said antibody of interest is selected from the group consisting of pathogenic anti-HLA antibodies, non-HLA pathogenic antibodies, non-HLA protective antibodies and combinations thereof;
   (2) when said pathogenic and/or protective antibody of interest is present in said biological sample, said pathogenic and/or protective antibody of interest binds to and forms a complex with each of said substrate conjugated to said antigen of said donor subject and said Fc receptor operatively linked to said detectable label; and
   (3) detection of said detectable label on said complex indicates that said biological sample contains said pathogenic and/or protective antibody of interest;
and further wherein, when said pathogenic and/or protective antibody of interest is detected in said biological sample from said donor subject, the method further comprises administering to said pre-transplant recipient subject who will receive an organ, cells, or tissue from said donor subject, a treatment selected from the group consisting of administering intravenous immune globulin preparations, a B cell depleting agent, a proteasome inhibitor, an anti-IL6 antibody, an anti-BAFF antibody and combinations thereof.

14. The method of claim 13, wherein an absence of detection of said detectable label indicates an absence of said complex in said biological sample from said donor subject.

15. The method of claim 13, wherein said biological sample from said donor subject is suspected of having anti-HLA antibodies.

16. The method of claim 13, wherein said substrate is a solid substrate.

17. The method of claim 13, wherein said Fc receptor is a recombinant Fc receptor expressed by an immune cell.

18. The method of claim 13, wherein said biological sample from said donor subject is contacted to said substrate conjugated to said antigen of said donor recipient prior to contact with said Fc receptor operatively linked to said detectable label.

19. The method of claim 18, wherein said biological sample from said donor subject that has been contacted to said substrate conjugated to said antigen of said donor recipient is washed prior to further contact with said Fc receptor operatively linked to said detectable label.

20. The method of claim 13, wherein said detectable label is biotin or a fluorochrome.

* * * * *